(12) United States Patent
Tulipano et al.

(10) Patent No.: US 8,076,281 B2
(45) Date of Patent: Dec. 13, 2011

(54) USE OF A GHRELIN AGONIST TO IMPROVE THE CATABOLIC EFFECTS OF GLUCOCORTICOID TREATMENT

(75) Inventors: Giovanni Tulipano, Cusago (IT); Andrea Giustina, Brescia (IT); Zheng Xin Dong, Holliston, MA (US); Michael DeWitt Culler, Hopkinton, MA (US)

(73) Assignee: IPSEN Pharma, S.A.S., Boulogne (FR)

( * ) Notice: Subject to any disclaimer, the term of this patent is extended or adjusted under 35 U.S.C. 154(b) by 359 days.

(21) Appl. No.: 12/283,161

(22) Filed: Sep. 10, 2008

(65) Prior Publication Data

US 2009/0163416 A1 Jun. 25, 2009

Related U.S. Application Data

(63) Continuation-in-part of application No. PCT/US2007/006042, filed on Mar. 9, 2007.
(60) Provisional application No. 60/781,172, filed on Mar. 10, 2006.

(51) Int. Cl.
*A61K 38/22* (2006.01)
(52) U.S. Cl. ............ 514/1.7; 514/4.8; 514/5.3; 514/8.6; 514/16.7; 514/21.3
(58) Field of Classification Search .......................... None
See application file for complete search history.

(56) References Cited

U.S. PATENT DOCUMENTS

| | | | |
|---|---|---|---|
| 7,385,026 B1 * | 6/2008 | Kangawa et al. ............ 530/324 |
| 7,666,833 B2 * | 2/2010 | Ghigo et al. .................... 514/1.1 |
| 2004/0092733 A1 * | 5/2004 | Burton et al. ..................... 540/5 |
| 2005/0143448 A1 * | 6/2005 | Grenard et al. ............... 514/454 |
| 2005/0158325 A1 * | 7/2005 | Hammerbeck et al. ..... 424/155.1 |
| 2005/0272648 A1 | 12/2005 | Dong et al. |
| 2006/0025566 A1 | 2/2006 | Hoveyda et al. |

FOREIGN PATENT DOCUMENTS

| EP | 1506786 A1 * | 2/2005 |
|---|---|---|
| WO | 97/24369 | 7/1997 |
| WO | 2004/009616 | 1/2004 |

OTHER PUBLICATIONS

Huysman et al. A Randomized, Placebo-Controlled GH Trial in Very Preterm Infants . . . Pediatric Research. 2005, vol. 58, No. 4, pp. 705-712.*
Leal-Cerro et al. Ghrelin is No Longer Able to Stimulate Growth Hormone Secretion . . . Clinical Neuroendocrinology. 2002, vol. 76, pp. 390-396.*
Barnes, P. J., "Inhaled Glucocorticoids for Asthma," NEJM, 1995, 332:868-875.

(Continued)

*Primary Examiner* — Jeffrey E Russel
(74) *Attorney, Agent, or Firm* — Yankwich & Associates; Alan F. Feeney; Pamela C. Ball

(57) ABSTRACT

A method and pharmaceutical composition for inhibiting the effect of glucocorticoids, particularly dexamethasone, which suppress growth hormone secretion, by administering ghrelin or a ghrelin analogue, for example, [Aib$^2$, Glu$^3$(NH-hexyl)] hGhrelin(1-28)-NH$_2$ (SEQ ID NO:2) or other suitable ghrelin agonist, to counteract the catabolic effects of said dexamethasone and other natural glucocorticoids.

20 Claims, 6 Drawing Sheets

OTHER PUBLICATIONS

Laron, Z. et al., "Intranasal administration of the GHRP hexarelin accelerates growth in short children," Clinical Endo., 1995, 43:631-635.

Reid, I. R., "Glucocorticoid osteoporosis—mechanisms and management," European J. Endo., 1997, 137:209-217.

Weiler, H. A. et al., "Longitudinal assessment of growth and bone mineral accretion in prematurely born infants treated for chronic lung disease with dexamethasone," Early Human Dev., 1997, 47:271-286.

* cited by examiner

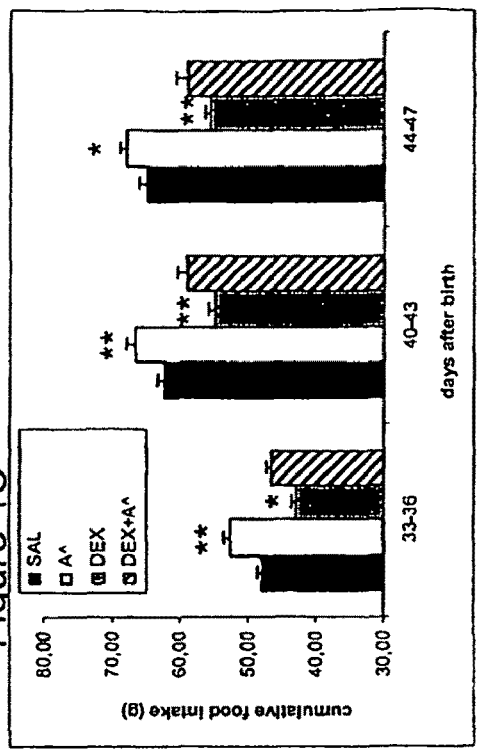
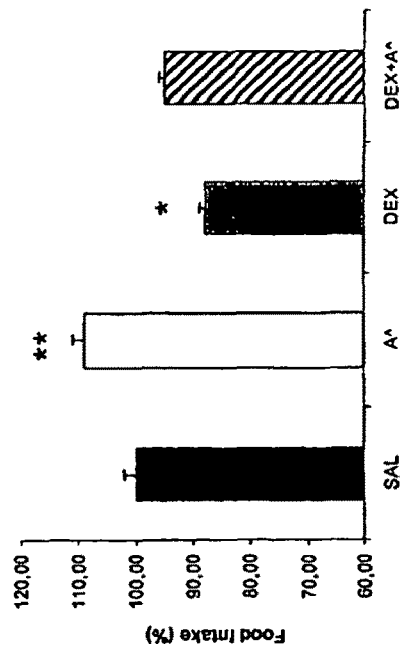
Figure 4C
^ A= [Aib2, Glu3(NH-hexyl)]hGhrelin(1-28)-NH2
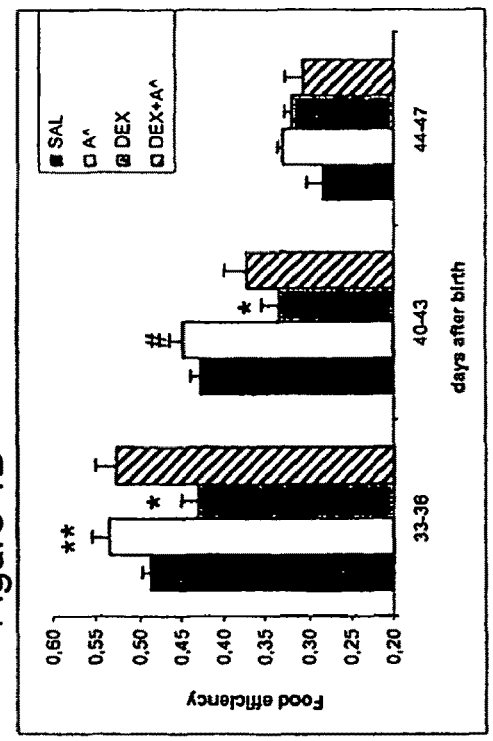

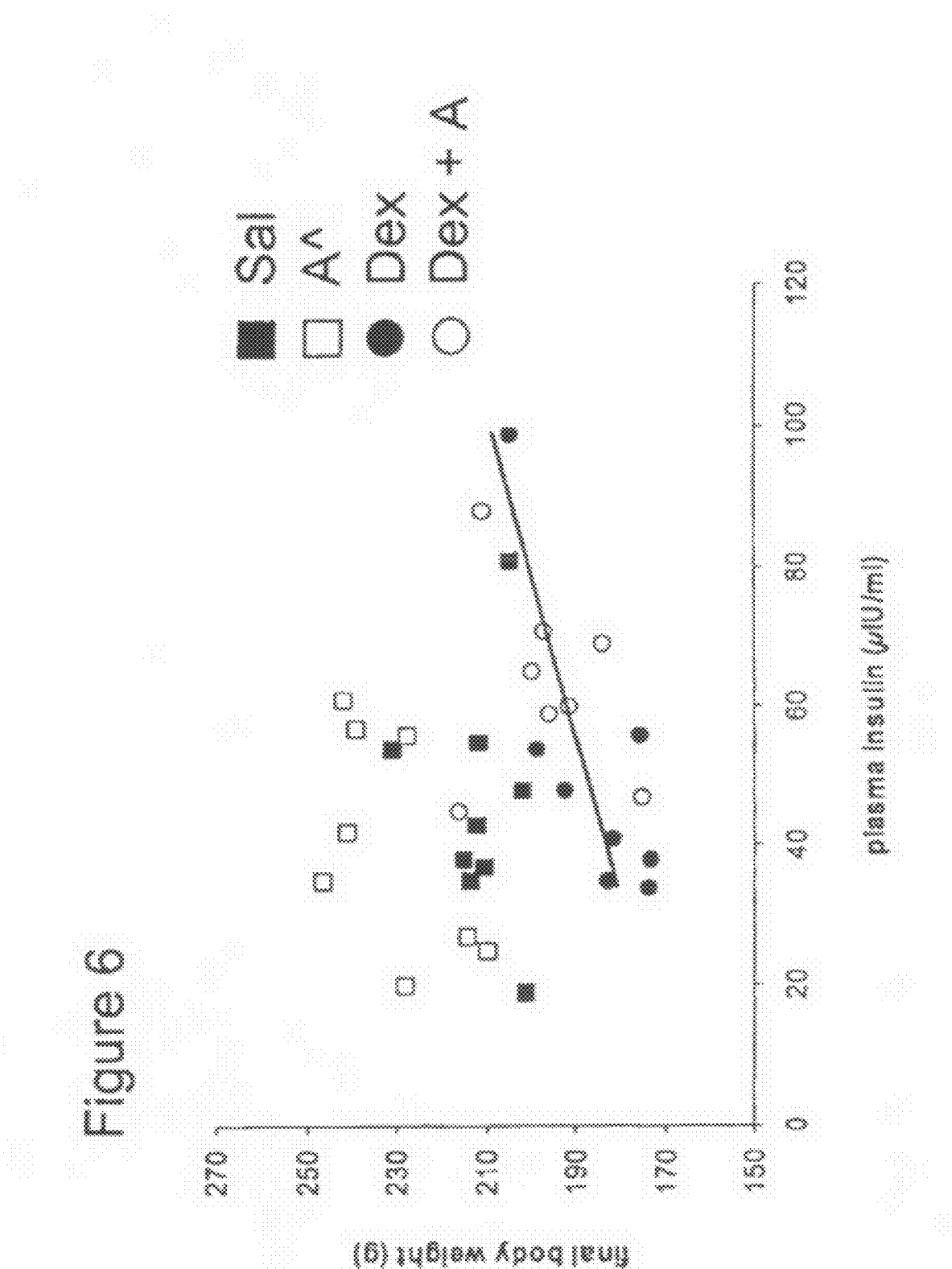

USE OF A GHRELIN AGONIST TO IMPROVE THE CATABOLIC EFFECTS OF GLUCOCORTICOID TREATMENT

This application is a continuation-in-part of copending international (PCT) application No. PCT/US2007/006042, filed Mar. 9, 2007, designating the United States, which application claims priority to U.S. provisional application 60/781,172 filed Mar. 10, 2006.

BACKGROUND OF THE INVENTION

Glucocorticoids are a class of steroid hormones characterized by an ability to bind with the cortisol receptor and trigger similar effects. Glucocorticoids have potent anti-inflammatory and immunosuppressive properties and as such are the best-known class of anti-inflammatory active ingredients. Owing to their broad range of uses and their great anti-inflammatory action, corticoid preparations are therapeutic agents of first choice in a wide variety of inflammatory diseases, such as, for example, diseases of the rheumatoid group, allergies, inflammatory diseases of the lungs, heart, and intestines, bronchial asthma, hyperproliferative diseases of the skin (psoriasis), eczemas, auto-immune diseases, or states of shock.

Dexamethasone, a synthetic member of the glucocorticoid class of hormones which exhibits anti-inflammatory and immunosuppressive properties which are 40 times more potent than naturally-occurring hydrocortisone and having the following structure,

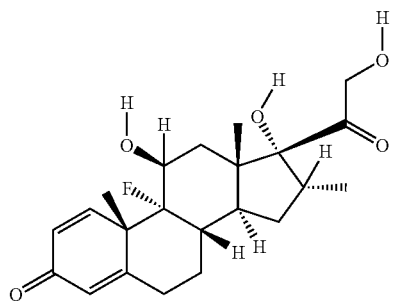

9-fluoro-11β, 17, 21-trihydroxy-16a-methylpregna-1,4-diene-3,20-dione, has been shown to augment the antiemetic effect of 5-HT$_3$ receptor antagonists. Dexamethasone is used to treat many inflammatory and autoimmune conditions, such as rheumatoid arthritis. It is also given to cancer patients undergoing chemotherapy to counteract certain side-effects.

Glucocorticoids, particularly dexamethasone, have been used for years to treat preterm infants who have or are at risk for chronic lung disease (The, T. F. et al., *Early Postnatal Dexamethasone Therapy for the Prevention of Chronic Lung Disease in Preterm Infants with Respiratory Distress Syndrome: A Multicenter Clinical Trial*, 1997, 100:715-6). These agents often have the short-term benefits of improving lung compliance and facilitating early weaning from mechanical ventilation. Newborns, with extremely low birth weight (ELBW), traditionally receive early postnatal dexamethasone therapy to treat and/or prevent severe respiratory distress syndrome and the subsequent onset of chronic lung disease.

Glucocorticoids, however, suppress growth hormone secretion. Human growth hormone (also may be referred to herein as "GH") is a single-chain polypeptide consisting of 191 amino acids (molecular weight 21,500). Disulfide bonds link positions 53 and 165 and positions 182 and 189 (Niall, *Nature, New Biology*, (1971), 230: 90). Effects of growth hormone on the tissues of the body can generally be described as anabolic (building up). Like most other protein hormones, GH acts by interacting with a specific receptor on the surface of cells. Height growth in childhood is the best known effect of GH action. GH also stimulates production of insulin-like growth factor 1 (may also be referred to herein as "IGF-1") which demonstrates growth-stimulating effects on a wide variety of tissues. GH also serves many other metabolic functions such as increasing calcium retention and mineralization in bones, increasing muscle mass by inducing protein synthesis, stimulating the immune system, reducing liver uptake of glucose thus contributing to the maintenance and function of pancreatic islets and promoting lipolysis, which results in some reduction of adipose tissue (body fat) and rising amounts of free fatty acids and glycerol in the blood.

The pulsatile release of growth hormone from the pituitary somatotrops is regulated by two hypothalamic neuropeptides: growth hormone-releasing hormone and somatostatin. Growth hormone-releasing hormone stimulates release of growth hormone whereas somatostatin inhibits secretion of growth hormone (Frohman et al., *Endocrinology Review* (1986) 7:223-53 and Strobi et al., *Pharmacology Review* (1994) 46:1-34). Most GH deficiencies are caused by defects in GH release, not primary defects in pituitary synthesis of the hormone itself. Increasing GH secretion can be achieved by stimulating or inhibiting various neurotransmitter systems in the brain and hypothalamus. As a result, the development of synthetic growth hormone-releasing agents to stimulate pituitary GH secretion is being pursued and may have several advantages over expensive and inconvenient GH replacement therapy. By acting along physiologic regulatory pathways, the most desirable agents would stimulate pulsatile GH secretion, and excessive levels of GH that have been associated with the undesirable side effects of exogenous GH administration would be avoided by virtue of intact negative feedback loops.

It is hypothesized that the pathogenesis of glucocorticoid mediated growth inhibition is most likely multifactorial in nature involving, partial growth hormone resistance, suppression of IGF-1 activity, and antagonism of insulin activity. These factors all influence carbohydrate and lipid metabolism.

By inhibiting GH secretion, elevated glucocorticoid levels can induce protein catabolism which in turn can lead to the degradation of skeletal muscle or the atrophy of intestinal villi. Deficiency in growth hormone results in a variety of medical disorders. The consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced.

Concern has been expressed regarding the effects of early dexamethasone therapy on somatic growth because glucocorticoids have been shown to alter cell size and DNA synthesis in animal models (Cotterrell M. et al., *Effects of Corticosteroids on the Biochemical Maturation of Rat Brain: Postnatal Cell Formation*, J. Neurochem., 1972, 19:2151-67). In addition, it has been found that dexamethasone therapy may compromise the accretion of bone mineral and this affect the velocity of bone growth, even when energy intake increases (Weiler, H. A. et al., *Longitudinal Assessment of Growth and Bone Mineral Accretion in Prematurely Born Infants Treated for Chronic Lung Disease with Dexamethasone*, Early Hum. Dev., 1997, 47:271-86 and Gibson, A. T. et al., *Growth Retar-* dation *After Dexamethasone Administration: Assessment by Knemometry*, Arch. Dis. Child, 1993, 69:505-9).

As reported in the *New England Journal of Medicine*, children who received early postnatal dexamethasone therapy for severe respiratory distress of prematurity were observed to have more neuromotor and cognitive function impairment and disability at school age than premature children not treated with dexamethasone. A study conducted at the China Medical University, Taichung, Taiwan, revealed that children treated with dexamethasone had significantly smaller head circumference and significantly lower mean height. In addition, dexamethasone-treated children were observed to evidence significantly poorer motor skills and motor coordination as well as poorer visual-motor integration as compared to children not treated with dexamethasone. The observed increase in neurodevelopmental dysfunction in neonates treated with dexamethasone led the Taiwanese researchers to recommend the discontinuation of use of a dexamethasone regimen to chronic lung disease in children despite its benefits due to its adverse effects on somatic growth at school age (Hendry, J., *Postnatal Dexamethasone Treatment Associate with Later Neuromotor and Cognitive Function Impairment and Disability*, 2004, N. England J. Med., 350:1304-13).

Glucocorticoid therapy is considered essential to the management of asthma; such treatments are often given on a daily basis and for an extended period of time. Recent studies have shown that glucocorticoid administration, while alleviating some symptoms of asthma, may also lead to airway damage or airway remodeling (see Dorscheid, D. R. et al., "*Apoptosis of airway epithelial cells induced by corticosteroids*", Am. J. Respir. Crit. Care Med., 2001, 164:1939-1947). As noted by Dorscheid, treatment of asthma with corticosteroids such as dexamethasone and the resulting induction of cell death "raises the possibility that at least one of the major components of chronic airway damage in asthma, epithelial shedding and denudation, may in part result from a major therapy for the disease."

Patients who must take large doses of pharmacological glucocorticoids, such as dexamethasone, can develop Cushing's syndrome if exposed to high enough doses over an extended period of time. Cushing's syndrome is a condition which is associated with a number of negative catabolic effects, including reduced growth velocity and lean body mass. A person suffering from Cushing's syndrome usually has a large, round face (commonly referred to as a "moon face") with slender arms and legs in proportion to the thickened trunk. The catabolic effects of this disease results in limited muscle capacity which leads to pronounced physical weakness. The skin becomes thin, bruises easily and heals poorly when bruised or cut. The heightened glucocorticoid levels associated with Cushing's syndrome, over time, results in chronic, elevated blood pressure, osteoporosis, diminished resistance to infections, the development of kidney stones and diabetes. Mental disturbances, including depression and hallucinations, have been found to occur in persons having Cushing's syndrome. Women usually experience irregular menstrual cycles. Children with Cushing's syndrome grow slowly and remain short. In some people, the adrenal glands also produce large amounts of androgens. Chronic glucocorticoid excess associated with Cushing's syndrome, left untreated, increases the risk of premature death.

Ghrelin likely enhances the activity of growth hormone releasing hormone (GHRH)-secreting neurons while concomitantly acting as a functional somatostatin (SS) antagonist (Ghigo, E. et al., *Eur J Endocrinol* (1997) 136(5):445-60). The observed ability of ghrelin to enhance food intake, increase food assimilation and gastric emptying, together with its ability to increase GH levels, thus promoting prompt nutrient incorporation into muscle and fat reserves, indicates that ghrelin may have therapeutic potential to treat indications wherein protein catabolism is a symptom.

Long-term administration of glucocorticoids is one of the most used treatments in clinical medicine but is known to suppress GH secretion and action. In fact, glucocorticoids inhibit pulsatile GH release, reduce GH receptor expression and signal transduction and inhibit IGF-1 bioactivity. Recognition of glucocorticoid-mediated antagonism of GH secretion and action has renewed interest in GH therapy or treatments to stimulate GH release as a potential means to reverse some of the most harmful side effects of glucocorticoid long-term treatment, such as growth inhibition and catabolic effects. Different studies suggest that the detrimental effects of glucocorticoid can be variably overcome by GH treatment, but long-term GH therapy also has the potential for adverse effects and requires further surveillance and study. It has been extensively demonstrated in humans and animals that the inhibitory effects of long-term glucocorticoid administration on GH secretion are mediated by increased somatostatin tone. Synthetic GHS appear to stimulate GH release, in part, through inhibition of somatostatin pathway; indeed, GHRP-6 is able to completely counteract glucocorticoid-mediated GH-inhibition in the rat.

It is a primary objective in the art to maximize the beneficial effects of glucocorticoids, in particular dexamethasone, while minimizing their adverse effects. The catabolic side effects of glucocorticoids prevent this class of substances from being put to an even broader range of therapeutic uses. Despite the reduced side-effect potential of modern corticoids, especially long-term treatment with active ingredients of this class of substances remains critical. Thus, there exists in the art the need for agents and methods to counteract the negative effects of and, thus to enhance the beneficial effects of, the long term administration of glucocorticoids.

SUMMARY OF THE INVENTION

This invention relates to a method and pharmaceutical composition for inhibiting the effect of glucocorticoids on growth hormone secretion, and more particularly to the pharmaceutical administration comprising a ghrelin analog, for example, [Aib$^2$, Glu$^3$(NH-hexyl)]hGhrelin(1-28)-NH$_2$ (SEQ ID NO:2), which has been found useful as a ghrelin agonist to counteract the catabolic effects of dexamethasone and other natural glucocorticoids.

Ghrelin is a naturally-occurring peptide having the following sequence: H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (Kojima M. et al. *Nature* (1999) 402(6762):656-60; SEQ ID NO:1). Ghrelin is produced by epithelial cells lining the fundus of the stomach which stimulate appetite and adiposity. Ghrelin levels are increased prior to a meal and decreased thereafter. Ghrelin levels in the plasma of obese individuals are lower than those in leaner individuals and levels of ghrelin increases during the time of the day from midnight to dawn in thinner individuals suggesting a flaw in the circulatory systems of obese individuals (Yildiz, B. et al., *Proc. Natl. Acad. Sci. USA* (2004) 101:10434-9) thus leading to the belief that ghrelin has the ability to regulate homeostasis.

Ghrelin was discovered to powerfully stimulate growth hormone secretion from the anterior pituitary gland and is believed to be an endogenous ligand for the GH secretagogues (GHS) subtype-1a receptor (hereinafter may be referred to as "GHS-1a"; Kojima et al., *Nature* (1999) 402: 656-60) both in animals and in humans (Ukkola, O et al., 2002 *Ann. Med.* (2002) 34:102-8).

In a first embodiment, the invention provides a method to ameliorate the catabolic effects of excess glucocorticoids in an individual in need of such treatment comprising administering to the individual a therapeutically effective amount of a ghrelin agonist. In one aspect of said first embodiment, the ghrelin agonist is [$Aib^2$, $Glu^3$(NH-hexyl)]hGhrelin(1-28)-$NH_2$ (SEQ ID NO:2). In another aspect, the ghrelin agonist useful for any of the methods described herein is selected from the group consisting of:

(Dap³(octanesulfonyl))hGhrelin(1-28)-NH₂; (SEQ ID NO: 3)

(Aib², A6c⁵)hGhrelin(1-28)-NH₂; (SEQ ID NO: 4)

(Aib²,⁶)hGhrelin(1-28)-NH₂; (SEQ ID NO: 5)

(Aib², 3-Pal⁹)hGhrelin(1-28)-NH₂; (SEQ ID NO: 6)

(A5c²)hGhrelin(1-28)-NH₂; (SEQ ID NO: 7)

(Act²)hGhrelin(1-28)-NH₂; (SEQ ID NO: 8)

(Aib², Act⁶)hGhrelin(1-28)-NH₂; (SEQ ID NO: 9)

(Aib², Abu⁶)hGhrelin(1-28)-NH₂; (SEQ ID NO: 10)

(Aib², 4-Hyp⁷)hGhrelin(1-28)-NH₂; (SEQ ID NO: 11)

(Aib², Thz⁷)hGhrelin(1-28)-NH₂; (SEQ ID NO: 12)

(Aib², Pip⁷)hGhrelin(1-28)-NH₂; (SEQ ID NO: 13)

(Aib², Dhp⁷)hGhrelin(1-28)-NH₂; (SEQ ID NO: 14)

(Aib²,⁸)hGhrelin(1-28)-NH₂; (SEQ ID NO: 15)

(Aib², 4-Pal⁹)hGhrelin(1-28)-NH₂; (SEQ ID NO: 16)

(Aib², Taz⁹)hGhrelin(1-28)-NH₂; (SEQ ID NO: 17)

(Aib²,¹⁰)hGhrelin(1-28)-NH₂; (SEQ ID NO: 18)

(Aib², Tic⁷)hGhrelin(1-28)-NH₂; (SEQ ID NO: 19)

(A6c⁵)hGhrelin(1-28)-NH₂; (SEQ ID NO: 20)

(3-Pal⁹)hGhrelin(1-28)-NH₂; (SEQ ID NO: 21)

(Aib⁸)hGhrelin(1-28)-NH₂; (SEQ ID NO: 22)

(2-Thi⁹)hGhrelin(1-28)-NH₂; (SEQ ID NO: 23)

(Aib², Cha⁵)hGhrelin(1-28)-NH₂; (SEQ ID NO: 24)

(Aib², Glu³(NH-hexyl), 4-Hyp⁷)hGhrelin(1-28)-NH₂; (SEQ ID NO: 25)

((Aib²,⁸, Glu³(NH-hexyl))hGhrelin(1-28)-NH₂; (SEQ ID NO: 26)

(Aib², Glu³(NH-hexyl), 3-Pal9)hGhrelin(1-28)-NH₂; (SEQ ID NO: 27)

(Aib², Glu³(NH-hexyl), 4-Pal9)hGhrelin(1-28)-NH₂; (SEQ ID NO: 28)

(Aib², Glu³(NH-hexyl), Taz⁹)hGhrelin(1-28)-NH₂; (SEQ ID NO: 29)

(Aib², Glu³(NH-hexyl), 2-Thi⁹)hGhrelin(1-28)-NH₂; (SEQ ID NO: 30)

(Aib²,¹⁰, Glu³(NH-hexyl))hGhrelin(1-28)-NH₂; (SEQ ID NO: 31)

(Glu³(NH-hexyl), 4-Hyp⁷)hGhrelin(1-28)-NH₂; (SEQ ID NO: 32)

(Glu³(NH-hexyl), Aib⁸)hGhrelin(1-28)-NH₂; (SEQ ID NO: 33)

(Aib²,¹², Glu³(NH-hexyl), 4-Pal⁹, Orn¹⁵)hGhrelin(1-28)-NH₂; (SEQ ID NO: 34)

(Glu³(O-hexyl))hGhrelin(1-28)-NH₂; (SEQ ID NO: 35)

(Aib²)hGhrelin(1-28)-NH₂; (SEQ ID NO: 36)

(Glu³(NH-hexyl))hGhrelin(1-28)-NH₂; (SEQ ID NO: 37)

(Ac-Gly¹, Aib²)hGhrelin(1-28)-NH₂; (SEQ ID NO: 38)

(n-butyryl-Gly¹)hGhrelin(1-28)-NH₂; (SEQ ID NO: 39)

(isobutyryl-Gly¹)hGhrelin(1-28)-NH₂; (SEQ ID NO: 40)

(n-octanoyl-Gly¹)hGhrelin(1-28)-NH₂; (SEQ ID NO: 41)

Cys³(S(CH₂)₉CH₃)hGhrelin(1-28)-NH₂; (SEQ ID NO: 42)

(Lys⁵)hGhrelin(1-28)-NH₂ (SEQ ID NO: 43)

Inp-D-2-Nal-D-Trp-Phe-Lys-NH₂ (SEQ ID NO: 44)

H-Inp-D-1-Nal-D-Trp-3-Pal-Lys-NH₂; (SEQ ID NO: 45)

H-Inp-D-2-Nal-D-Trp-Orn-Lys-NH₂; (SEQ ID NO: 46)

H-Inp-D-Bip-D-Trp-Phe-Lys-NH₂; (SEQ ID NO: 47)

H-Inp-D-2-Nal-D-Trp-Pff-Lys-NH₂; (SEQ ID NO: 48)

H-Inp-D-2-Nal-D-Trp-2-Thi-Lys-NH₂; (SEQ ID NO: 49)

H-Inp-D-2-Nal-D-Trp-Taz-Lys-NH₂; (SEQ ID NO: 50)

H-Inp-D-Dip-D-Trp-Phe-Lys-NH$_2$; (SEQ ID NO: 51)

H-Inp-D-Bpa-D-Trp-Phe-Lys-NH$_2$; (SEQ ID NO: 52)

H-Inp-D-2-Nal-D-Bpa-Phe-Lys-NH$_2$; (SEQ ID NO: 53)

H-Inp-D-2-Nal-D-Trp-3-Pal-NH$_2$; (SEQ ID NO: 54)

H-Inp-D-2-Nal-D-Trp-4-Pal-NH$_2$; (SEQ ID NO: 55)

H-Inp-D-1-Nal-D-Trp-3-Pal-NH$_2$; (SEQ ID NO: 56)

H-Inp-D-Bip-D-Trp-Phe-NH$_2$; (SEQ ID NO: 57)

H-Inp-D-2-Nal-D-Trp-Thr(Bzl)-NH$_2$; (SEQ ID NO: 58)

H-Inp-D-2-Nal-D-Trp-Pff-NH$_2$; (SEQ ID NO: 59)

H-Inp-D-2-Nal-D-Trp-2-Thi-NH$_2$; (SEQ ID NO: 60)

H-Inp-D-2-Nal-D-Trp-Taz-NH$_2$; (SEQ ID NO: 61)

H-Inp-D-Dip-D-Trp-Phe-NH$_2$; (SEQ ID NO: 61)

H-Inp-D-Dip-D-Trp-Phe-NH$_2$; (SEQ ID NO: 62)

H-Inp-D-2-Nal-D-Dip-Phe-NH$_2$; (SEQ ID NO: 63)

H-Inp-D-Bal-D-Trp-Phe-NH$_2$; (SEQ ID NO: 64)

H-Inp-D-2-Nal-D-Bal-Phe-NH$_2$; (SEQ ID NO: 65)

H-Inp-D-2-Nal-D-Trp-3-Pal-Lys-NH$_2$; (SEQ ID NO: 66)

H-Inp-D-Trp-D-2-Nal($\Psi$)-Pim; (SEQ ID NO: 67)

H-Inp-D-Bal-D-Trp-2-Thi-Lys-NH$_2$; (SEQ ID NO: 68)

H-Inp-D-Bal-D-Trp-Phe-Lys-NH$_2$; (SEQ ID NO: 69)

H-Inp-D-1-Nal-D-Trp-2-Thi-Lys-NH$_2$; (SEQ ID NO: 7)

H-Inp-D-2-Nal-D-Trp-Phe-Apc-NH$_2$; (SEQ ID NO: 71)

H-Inp-D-1-Nal-D-Trp-Phe-Apc-NH$_2$; (SEQ ID NO: 72)

H-Inp-D-Bal-D-Trp-Phe-Apc-NH$_2$; (SEQ ID NO: 73)

H-Apc-D-2-Nal-D-Trp-Phe-Lys-NH$_2$; (SEQ ID NO: 74)

H-Apc-D-1-Nal-D-Trp-2-Thi-Lys-NH$_2$; (SEQ ID NO: 75)

H-Inp-D-1-Nal-D-Trp-2-Thi-NH$_2$; (SEQ ID NO: 76)

H-Apc-D-1-Nal-D-Trp-Phe-NH$_2$; (SEQ ID NO: 77)

H-Inp-D-2-Nal-D-Trp($\Psi$)-Pim; (SEQ ID NO: 78)

H-Inp-D-1-Nal-D-Trp($\Psi$)-Pim; (SEQ ID NO: 79)

H-Inp-D-Bal-D-Trp($\Psi$)-Pim; (SEQ ID NO: 80)

H-Aib-D-Ser(Bzl)-D-Trp($\Psi$)-Pim; (SEQ ID NO: 81)

H-Inp-D-1-Nal-D-Trp-Taz-Lys-NH$_2$; (SEQ ID NO: 82)

H-Inp-D-Bal-D-Trp-Taz-Lyz-NH$_2$; (SEQ ID NO: 83)

H-Apc-D-1-Nal-D-Trp-Taz-Lys-NH$_2$; (SEQ ID NO: 84)

H-Apc-D-Bal-D-Trp-Taz-Lys-NH$_2$; (SEQ ID NO: 85)

H-Apc-D-Bal-D-Trp-2-Thi-Lys-NH$_2$; (SEQ ID NO: 86)

H-Apc-D-Bal-D-Trp-Phe-Lys-NH$_2$; (SEQ ID NO: 87)

H-Apc-D-1-Nal-D-Trp-Phe-Apc-NH$_2$; (SEQ ID NO: 88)

H-Apc-D-Bal-D-Trp-Phe-Apc-NH$_2$; (SEQ ID NO: 89)

H-Apc-D-1-Nal-D-1-Nal-Phe-Apc-NH$_2$; (SEQ ID NO: 90)

H-Apc-D-1-Nal-D-2-Nal-Phe-Apc-NH$_2$; (SEQ ID NO: 91)

H-Apc-D-1-Nal-D-1-Nal-Phe-Lys-NH$_2$; (SEQ ID NO: 92)

H-Apc-D-Bal-D-1-Nal-Phe-Apc-NH$_2$; (SEQ ID NO: 93)

H-Apc-D-Bal-D-2-Nal-Phe-Apc-NH$_2$; (SEQ ID NO: 94)

H-Apc-D-Bal-D-2-Nal-Phe-Lys-NH$_2$; (SEQ ID NO: 95)

H-Apc-D-1-Nal-D-Trp-2-Thi-NH$_2$; (SEQ ID NO: 96)

H-Apc-D-Bal-D-Trp-Phe-NH$_2$; (SEQ ID NO: 97)

H-Apc-D-1-Nal-D-Trp-Taz-NH$_2$; (SEQ ID NO: 98)

H-Apc-D-Bal-D-Trp-2-Thi-NH$_2$; (SEQ ID NO: 99)

H-Apc-D-Bal-D-Trp-Taz-NH$_2$; (SEQ ID NO: 100)

H-Apc-D-2-Nal-D-Trp-2-Thi-NH$_2$; (SEQ ID NO: 101)

H-Apc-D-2-Nal-D-Trp-Taz-NH$_2$; (SEQ ID NO: 102)

H-Inp-D-1-Nal-D-Trp-Taz-Apc-NH$_2$; (SEQ ID NO: 103)

-continued

H-Inp-D-Bal-D-Trp-Taz-Apc-NH$_2$; (SEQ ID NO: 104)

H-Apc-D-1-Nal-D-Trp-Taz-Apc-NH$_2$; (SEQ ID NO: 105)

H-Apc-D-Bal-D-Trp-Taz-Apc-NH$_2$; (SEQ ID NO: 106)

H-Inp-D-2-Nal-D-Trp-4-Pal-Lys-NH$_2$; (SEQ ID NO: 107)

H-Inp-D-2-Nal-D-Trp-Thr(Bzl)-Lys-NH$_2$; (SEQ ID NO: 108)

H-Apc-D-Bal-D-1-Nal-Phe-Lys-NH$_2$; (SEQ ID NO: 109)

H-Inp-D-1-Nal-D-Trp-2-Thi-Apc-NH$_2$; (SEQ ID NO: 110)

H-Inp-D-Bal-D-Trp-2-Thi-Apc-NH$_2$; (SEQ ID NO: 111)

H-Apc-D-1-Nal-D-Trp-2-Thi-Apc-NH$_2$; (SEQ ID NO: 112)

H-Apc-D-Bal-D-Trp-2-Thi-Apc-NH$_2$; or (SEQ ID NO: 113)

H-Apc-D-1-Nal-D-Trp-Phe-Lys-NH$_2$ (SEQ ID NO: 114)

(Aib$^{2,8}$, Glu(NH-hexyl)$^{3,17}$)hGhrelin(1-28)-NH$_2$; (SEQ ID NO: 115)

(Inp$^1$, Aib$^{2,10}$, Glu(NH-hexyl)$^3$)hGhrelin(1-28)-NH$_2$; (SEQ ID NO: 116)

(1-Apc$^1$, Aib$^{2,10}$, Glu(NH-hexyl)$^3$)-hGhrelin(1-28)-NH$_2$; (SEQ ID NO: 117)

(Inp$^1$)hGhrelin(1-28)-NH$_2$; (SEQ ID NO: 118)

(Inp$^1$, Aib$^2$)hGhrelin(1-28)-NH$_2$; (SEQ ID NO: 119)

(Inp$^1$, Aib$^2$, Glu(NH-hexyl)$^3$)hGhrelin(1-28)-NH$_2$; (SEQ ID NO: 120)

(Inp$^1$, Aib$^{2,10}$)hGhrelin(1-28)-NH$_2$; (SEQ ID NO: 121)

(Inp$^1$, Aib$^{2,8}$)hGhrelin(1-28)-NH$_2$; (SEQ ID NO: 122)

(Inp$^1$, Aib$^2$, Ser(n-octanoyl)$^{17}$)hGhrelin(1-28)-NH$_2$; (SEQ ID NO: 123)

(Inp$^1$, Ser(n-octanoyl)$^{17}$)hGhrelin(1-28)-NH$_2$; (SEQ ID NO: 124)

(Asp$^3$(NH-heptyl))hGhrelin(1-28)-NH$_2$ (SEQ ID NO: 125)

(des-Ser$^2$)hGhrelin(1-28)-NH$_2$; (SEQ ID NO: 126)

(des-Gly$^1$, des-Ser$^2$)hGhrelin(1-28)-NH$_2$; (SEQ ID NO: 127)

(Aib$^1$)hGhrelin(1-28)-NH$_2$; and (SEQ ID NO: 128)

(Asp$^3$(O-hexyl))hGhrelin(1-28)-NH$_2$. (SEQ ID NO: 129)

In another aspect of said first embodiment, the excess glucocorticoids are the result of a disease or a condition. In another aspect of said first embodiment, the excess glucocorticoids are the result of the long term administration of glucocorticoids to the individual. In a further aspect of the immediately foregoing, the administered glucocorticoid is dexamethasone. In another aspect of said first embodiment, the glucocorticoid induced catabolic effects include, but are not limited to, a reduction in growth, a reduction in growth rate, a reduction in body weight, a reduction in lean body mass, a reduction in IGF-1 levels and/or a reduction in bone mass. The individual receiving the method of the invention to ameliorate a reduction in growth, a reduction in growth rate, a reduction in body weight, a reduction in lean body mass, a reduction in IGF-levels and/or a reduction in bone mass is a child or an adult. In another embodiment, the ghrelin agonist useful to ameliorate a reduction in growth, a reduction in growth rate, a reduction in body weight, a reduction in lean body mass, a reduction in IGF-1 levels and/or a reduction in bone mass is [Aib$^2$, Glu$^3$(NH-hexyl)]hGhrelin(1-28)-NH$_2$ (SEQ ID NO:2) or other suitable ghrelin agonist.

In yet another embodiment, the reduction in growth, growth rate, body weight, lean body mass, IGF-1 levels and/or bone mass is a result of the administration of dexamethasone.

In another aspect of said first embodiment, the administration includes, but is not limited to, subcutaneous, intramuscular, intranasal, intraperitoneal, and intravenous administration.

In a second embodiment, the invention provides a method allowing for the long term administration of therapeutic doses of glucocorticoids to treat a disease or condition, comprising alleviating the catabolic effects of the administration of said long term therapeutic doses of glucocorticoids by the administration of a ghrelin agonist. In one aspect of said second embodiment, the ghrelin agonist is [Aib$^2$, Glu$^3$(NH-hexyl)]hGhrelin(1-28)-NH$_2$ (SEQ ID NO:2) or other suitable ghrelin agonist. In yet another aspect of said second embodiment, the glucocorticoid is dexamethasone. The individual receiving the method of the invention to alleviate the catabolic effects of long term administration of therapeutic doses of glucocorticoids, such as dexamethasone, by the administration of a ghrelin agonist, such as [Aib$^2$, Glu$^3$(NH-hexyl)]hGhrelin(1-28)-NH$_2$ (SEQ ID NO:2) or other suitable ghrelin agonist, is a child or an adult.

In another aspect of said second embodiment, the invention provides a method allowing for the long term administration of therapeutic doses of glucocorticoids to a child to treat respiratory distress of prematurity, comprising alleviating the catabolic effects of the administration of said long term therapeutic doses of glucocorticoids by the administration of a ghrelin agonist. In another aspect of the foregoing, the ghrelin agonist is [Aib$^2$, Glu$^3$(NH-hexyl)]hGhrelin(1-28)-NH$_2$ (SEQ ID NO:2) or other suitable ghrelin agonist. In yet another aspect of the foregoing, the glucocorticoid is dexamethasone.

In yet another aspect of said second embodiment, the invention provides a method allowing for the long term administration of therapeutic doses of glucocorticoids to treat asthma, comprising alleviating the catabolic effects of the administration of said long term therapeutic doses of glucocorticoids by the administration of a ghrelin agonist. In another aspect of the foregoing, the ghrelin agonist is [Aib$^2$, Glu$^3$(NH-hexyl)]hGhrelin(1-28)-NH$_2$ (SEQ ID NO:2) or other suitable ghrelin agonist. In yet another aspect of the foregoing, the glucocorticoid is dexamethasone. The individual receiving the method of the invention allowing the long term administration of therapeutic doses of glucocorticoids to treat asthma may be a child or an adult.

In yet another embodiment, the invention provides a method allowing for the long term administration of therapeutic doses of glucocorticoids to treat a disease or condition, comprising alleviating the catabolic effects of the administration of said long term therapeutic doses of glucocorticoids by the administration of a ghrelin agonist wherein the administration includes, but is not limited to, intramuscular, intranasal, intraperitoneal, and intravenous administration.

BRIEF DESCRIPTION OF THE DRAWINGS

FIG. 4. Panel A: the effect of the different pharmacological treatment on 24-h food intake expressed as a percent of the control value. Data represented the mean±SEM of nine determinations performed at irregular intervals from day 33 to day 47 after birth. Panel B: the effect of the different pharmacological treatments on food efficacy calculated as a ratio between food intake (g) and body weight (g) measured over the same time interval at different stages of growth. Data represents the mean±SEM of eight rats. *P<0.05; **<0.01 vs SAL-treated rats (Dunnett's t test). Panel C: the effect of the different pharmacological treatments on the cumulative food intake measured over the indicated time intervals at different stages of growth.

FIG. 6. Study of the relationship between the final body weight and plasma insulin concentration at the moment of the killing of the rats: a positive linear correlation was observed, limiting the analysis to DEX-treated rats (N=16, two tailed Pearson R=0.5848, P<0.05); dotted square, SAL; open square, [Aib$^2$, Glu$^3$(NH-hexyl)]hGhrelin(1-28)-NH$_2$ (SEQ ID NO:2); dotted circle, DEX; open circle, DEX+[Aib$^2$, Glu$^3$(NH-hexyl)]hGhrelin(1-28)-NH$_2$ (SEQ ID NO:2).

DETAILED DESCRIPTION OF THE INVENTION

Figure 1:
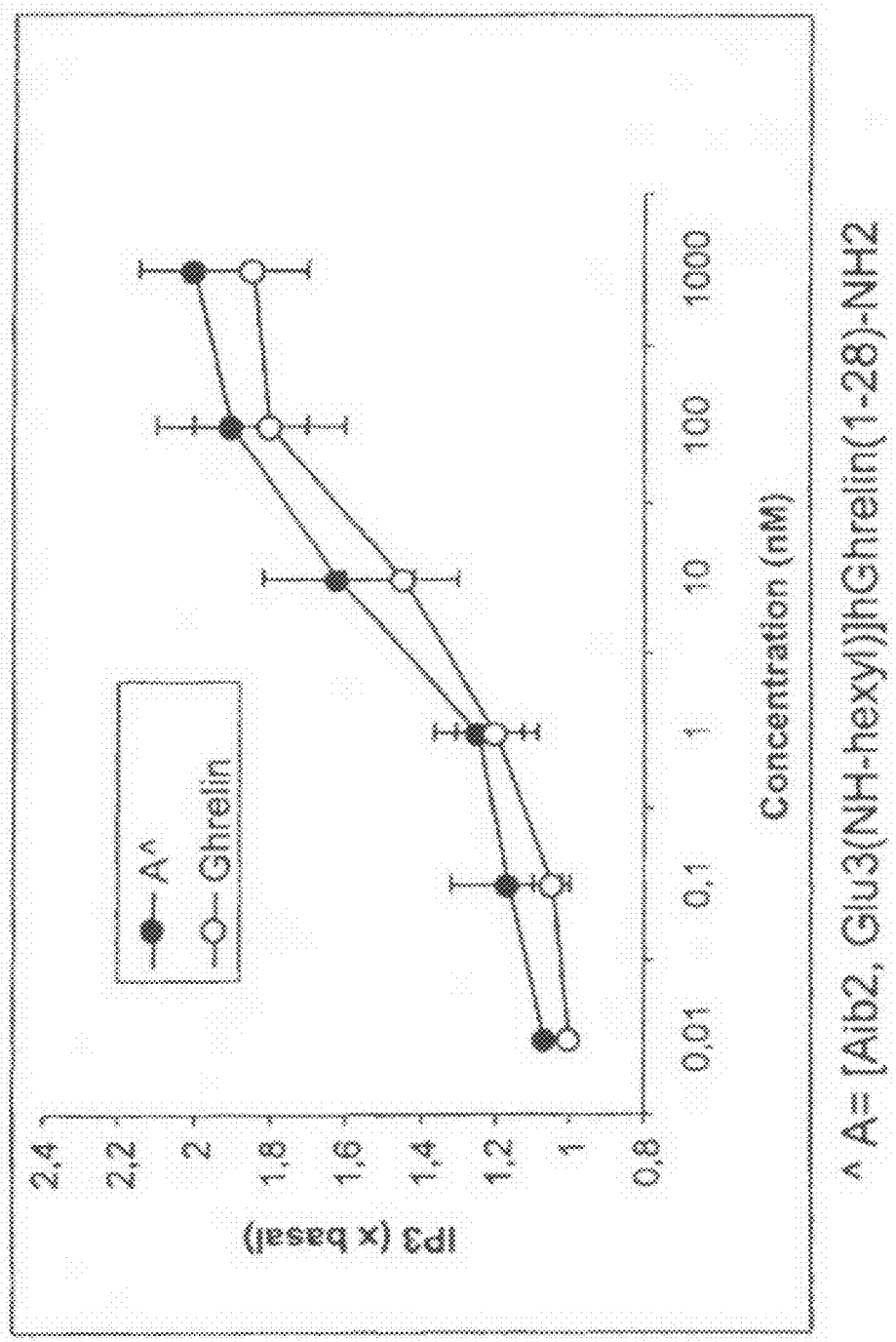
FIG. 1. Dose-response effects of [Aib$^2$, Glu$^3$(NH-hexyl)]hGhrelin(1-28)-NH$_2$ (SEQ ID NO:2) (indicated as "A") versus ghrelin on phosphoinositide turnover in transfected CHO-K1 cells expressing hGHS1a receptor. Results are the mean±SD of three independent experiments.

The inventors have devised a new method of treating catabolic dysfunctions induced by glucocorticoid excess. The present invention comprises the administration to a human or animal afflicted with, or likely to develop, a catabolic dysfunction, a therapeutically effective amount of ghrelin, or a functional analogue thereof, in particular [Aib$^2$, Glu$^3$(NH-hexyl)]hGhrelin(1-28)-NH$_2$ (SEQ ID NO:2). Additional suitable ghrelin analogues include:

(Dap$^3$(octanesulfonyl))hGhrelin(1-28)-NH$_2$;   (SEQ ID NO: 3)

(Aib$^2$, A6c$^5$)hGhrelin(1-28)-NH$_2$;   (SEQ ID NO: 4)

(Aib$^{2,6}$)hGhrelin(1-28)-NH$_2$;   (SEQ ID NO: 5)

(Aib$^2$, 3-Pal$^9$)hGhrelin(1-28)-NH$_2$;   (SEQ ID NO: 6)

(A5c$^2$)hGhrelin(1-28)-NH$_2$;   (SEQ ID NO: 7)

(Act$^2$)hGhrelin(1-28)-NH$_2$;   (SEQ ID NO: 8)

(Aib$^2$, Act$^6$)hGhrelin(1-28)-NH$_2$;   (SEQ ID NO: 9)

(Aib$^2$, Abu$^6$)hGhrelin(1-28)-NH$_2$;   (SEQ ID NO: 10)

(Aib$^2$, 4-Hyp$^7$)hGhrelin(1-28)-NH$_2$;   (SEQ ID NO: 11)

(Aib$^2$, Thz$^7$)hGhrelin(1-28)-NH$_2$;   (SEQ ID NO: 12)

(Aib$^2$, Pip$^7$)hGhrelin(1-28)-NH$_2$;   (SEQ ID NO: 13)

(Aib$^2$, Dhp$^7$)hGhrelin(1-28)-NH$_2$;   (SEQ ID NO: 14)

(Aib$^{2,8}$)hGhrelin(1-28)-NH$_2$;   (SEQ ID NO: 15)

(Aib$^2$, 4-Pal$^9$)hGhrelin(1-28)-NH$_2$;   (SEQ ID NO: 16)

(Aib$^2$, Taz$^9$)hGhrelin(1-28)-NH$_2$;   (SEQ ID NO: 17)

(Aib$^{2,10}$)hGhrelin(1-28)-NH$_2$;   (SEQ ID NO: 18)

(Aib$^2$, Tic$^7$)hGhrelin(1-28)-NH$_2$;   (SEQ ID NO: 19)

(A6c$^5$)hGhrelin(1-28)-NH$_2$;   (SEQ ID NO: 20)

(3-Pal$^9$)hGhrelin(1-28)-NH$_2$;   (SEQ ID NO: 21)

(Aib$^8$)hGhrelin(1-28)-NH$_2$;   (SEQ ID NO: 22)

(2-Thi$^9$)hGhrelin(1-28)-NH$_2$;   (SEQ ID NO: 23)

-continued (Aib⁵, Cha⁵)hGhrelin(1-28)-NH₂; (SEQ ID NO: 24)

(Aib², Glu³(NH-hexyl), 4-Hyp⁷)hGhrelin(1-28)-NH₂; (SEQ ID NO: 25)

((Aib²,⁸, Glu³(NH-hexyl))hGhrelin(1-28)-NH₂; (SEQ ID NO: 26)

(Aib², Glu³(NH-hexyl), 3-Pal9)hGhrelin(1-28)-NH₂; (SEQ ID NO: 27)

(Aib², Glu³(NH-hexyl), 4-Pal9)hGhrelin(1-28)-NH₂; (SEQ ID NO: 28)

(Aib², Glu³(NH-hexyl), Taz⁹)hGhrelin(1-28)-NH₂; (SEQ ID NO: 29)

(Aib², Glu³(NH-hexyl), 2-Thi⁹)hGhrelin(1-28)-NH₂; (SEQ ID NO: 30)

(Aib²,¹⁰, Glu³(NH-hexyl))hGhrelin(1-28)-NH₂; (SEQ ID NO: 31)

(Glu³(NH-hexyl), 4-Hyp⁷)hGhrelin(1-28)-NH₂; (SEQ ID NO: 32)

(Glu³(NH-hexyl), Aib⁸)hGhrelin(1-28)-NH₂; (SEQ ID NO: 33)

(Aib²,¹², Glu³(NH-hexyl), 4-Pal⁹, Orn¹⁵)hGhrelin(1-28)-NH₂; (SEQ ID NO: 34)

(Glu³(O-hexyl))hGhrelin(1-28)-NH₂; (SEQ ID NO: 35)

(Aib²)hGhrelin(1-28)-NH₂; (SEQ ID NO: 36)

(Glu³(NH-hexyl))hGhrelin(1-28)-NH₂; (SEQ ID NO: 37)

(Ac-Gly¹, Aib²)hGhrelin(1-28)-NH₂; (SEQ ID NO: 38)

(n-butyryl-Gly¹)hGhrelin(1-28)-NH₂; (SEQ ID NO: 39)

(isobutyryl-Gly¹)hGhrelin(1-28)-NH₂; (SEQ ID NO: 40)

(n-octanoyl-Gly¹)hGhrelin(1-28)-NH₂; (SEQ ID NO: 41)

Cys³(S(CH₂)₉CH₃)hGhrelin(1-28)-NH₂; (SEQ ID NO: 42)

(Lys⁵)hGhrelin(1-28)-NH₂ (SEQ ID NO: 43)

Inp-D-2-Nal-D-Trp-Phe-Lys-NH₂ (SEQ ID NO: 44)

H-Inp-D-1-Nal-D-Trp-3-Pal-Lys-NH₂; (SEQ ID NO: 45)

H-Inp-D-2-Nal-D-Trp-Orn-Lys-NH₂; (SEQ ID NO: 46)

H-Inp-D-Bip-D-Trp-Phe-Lys-NH₂; (SEQ ID NO: 47)

H-Inp-D-2-Nal-D-Trp-Pff-Lys-NH₂; (SEQ ID NO: 48)

H-Inp-D-2-Nal-D-Trp-2-Thi-Lys-NH₂; (SEQ ID NO: 49)

H-Inp-D-2-Nal-D-Trp-Taz-Lys-NH₂; (SEQ ID NO: 50)

H-Inp-D-Dip-D-Trp-Phe-Lys-NH₂; (SEQ ID NO: 51)

H-Inp-D-Bpa-D-Trp-Phe-Lys-NH₂; (SEQ ID NO: 52)

H-Inp-D-2-Nal-D-Bpa-Phe-Lys-NH₂; (SEQ ID NO: 53)

H-Inp-D-2-Nal-D-Trp-3-Pal-NH₂; (SEQ ID NO: 54)

H-Inp-D-2-Nal-D-Trp-4-Pal-NH₂; (SEQ ID NO: 55)

H-Inp-D-1-Nal-D-Trp-3-Pal-NH₂; (SEQ ID NO: 56)

H-Inp-D-Bip-D-Trp-Phe-NH₂; (SEQ ID NO: 57)

H-Inp-D-2-Nal-D-Trp-Thr(Bzl)-NH₂; (SEQ ID NO: 58)

H-Inp-D-2-Nal-D-Trp-Pff-NH₂; (SEQ ID NO: 59)

H-Inp-D-2-Nal-D-Trp-2-Thi-NH₂; (SEQ ID NO: 60)

H-Inp-D-2-Nal-D-Trp-Taz-NH₂; (SEQ ID NO: 61)

H-Inp-D-Dip-D-Trp-Phe-NH₂; (SEQ ID NO: 61)

H-Inp-D-Dip-D-Trp-Phe-NH₂; (SEQ ID NO: 62)

H-Inp-D-2-Nal-D-Dip-Phe-NH₂; (SEQ ID NO: 63)

H-Inp-D-Bal-D-Trp-Phe-NH₂; (SEQ ID NO: 64)

H-Inp-D-2-Nal-D-Bal-Phe-NH₂; (SEQ ID NO: 65)

H-Inp-D-2-Nal-D-Trp-3-Pal-Lys-NH₂; (SEQ ID NO: 66)

H-Inp-D-Trp-D-2-Nal(Ψ)-Pim; (SEQ ID NO: 67)

H-Inp-D-Bal-D-Trp-2-Thi-Lys-NH₂; (SEQ ID NO: 68)

H-Inp-D-Bal-D-Trp-Phe-Lys-NH₂; (SEQ ID NO: 69)

H-Inp-D-1-Nal-D-Trp-2-Thi-Lys-NH₂; (SEQ ID NO: 70)

H-Inp-D-2-Nal-D-Trp-Phe-Apc-NH₂; (SEQ ID NO: 71)

H-Inp-D-1-Nal-D-Trp-Phe-Apc-NH₂; (SEQ ID NO: 72)

H-Inp-D-Bal-D-Trp-Phe-Apc-NH₂; (SEQ ID NO: 73)

H-Apc-D-2-Nal-D-Trp-Phe-Lys-NH₂; (SEQ ID NO: 74)

H-Apc-D-1-Nal-D-Trp-2-Thi-Lys-NH₂; (SEQ ID NO: 75)

H-Inp-D-1-Nal-D-Trp-2-Thi-NH₂; (SEQ ID NO: 76)

H-Apc-D-1-Nal-D-Trp-Phe-NH$_2$; (SEQ ID NO: 77)

H-Inp-D-2-Nal-D-Trp(Ψ)-Pim; (SEQ ID NO: 78)

H-Inp-D-1-Nal-D-Trp(Ψ)-Pim; (SEQ ID NO: 79)

H-Inp-D-Bal-D-Trp(Ψ)-Pim; (SEQ ID NO: 80)

H-Aib-D-Ser(Bzl)-D-Trp(Ψ)-Pim; (SEQ ID NO: 81)

H-Inp-D-1-Nal-D-Trp-Taz-Lys-NH$_2$; (SEQ ID NO: 82)

H-Inp-D-Bal-D-Trp-Taz-Lyz-NH$_2$; (SEQ ID NO: 83)

H-Apc-D-1-Nal-D-Trp-Taz-Lys-NH$_2$; (SEQ ID NO: 84)

H-Apc-D-Bal-D-Trp-Taz-Lys-NH$_2$; (SEQ ID NO: 85)

H-Apc-D-Bal-D-Trp-2-Thi-Lys-NH$_2$; (SEQ ID NO: 86)

H-Apc-D-Bal-D-Trp-Phe-Lys-NH$_2$; (SEQ ID NO: 87)

H-Apc-D-1-Nal-D-Trp-Phe-Apc-NH$_2$; (SEQ ID NO: 88)

H-Apc-D-Bal-D-Trp-Phe-Apc-NH$_2$; (SEQ ID NO: 89)

H-Apc-D-1-Nal-D-1-Nal-Phe-Apc-NH$_2$; (SEQ ID NO: 90)

H-Apc-D-1-Nal-D-2-Nal-Phe-Apc-NH$_2$; (SEQ ID NO: 91)

H-Apc-D-1-Nal-D-1-Nal-Phe-Lys-NH$_2$; (SEQ ID NO: 92)

H-Apc-D-Bal-D-1-Nal-Phe-Apc-NH$_2$; (SEQ ID NO: 93)

H-Apc-D-Bal-D-2-Nal-Phe-Apc-NH$_2$; (SEQ ID NO: 94)

H-Apc-D-Bal-D-2-Nal-Phe-Lys-NH$_2$; (SEQ ID NO: 95)

H-Apc-D-1-Nal-D-Trp-2-Thi-NH$_2$; (SEQ ID NO: 96)

H-Apc-D-Bal-D-Trp-Phe-NH$_2$; (SEQ ID NO: 97)

H-Apc-D-1-Nal-D-Trp-Taz-NH$_2$; (SEQ ID NO: 98)

H-Apc-D-Bal-D-Trp-2-Thi-NH$_2$; (SEQ ID NO: 99)

H-Apc-D-Bal-D-Trp-Taz-NH$_2$; (SEQ ID NO: 100)

H-Apc-D-2-Nal-D-Trp-2-Thi-NH$_2$; (SEQ ID NO: 101)

H-Apc-D-2-Nal-D-Trp-Taz-NH$_2$; (SEQ ID NO: 102)

H-Inp-D-1-Nal-D-Trp-Taz-Apc-NH$_2$; (SEQ ID NO: 103)

H-Inp-D-Bal-D-Trp-Taz-Apc-NH$_2$; (SEQ ID NO: 104)

H-Apc-D-1-Nal-D-Trp-Taz-Apc-NH$_2$; (SEQ ID NO: 105)

H-Apc-D-Bal-D-Trp-Taz-Apc-NH$_2$; (SEQ ID NO: 106)

H-Inp-D-2-Nal-D-Trp-4-Pal-Lys-NH$_2$; (SEQ ID NO: 107)

H-Inp-D-2-Nal-D-Trp-Thr(Bzl)-Lys-NH$_2$; (SEQ ID NO: 108)

H-Apc-D-Bal-D-1-Nal-Phe-Lys-NH$_2$; (SEQ ID NO: 109)

H-Inp-D-1-Nal-D-Trp-2-Thi-Apc-NH$_2$; (SEQ ID NO: 110)

H-Inp-D-Bal-D-Trp-2-Thi-Apc-NH$_2$; (SEQ ID NO: 111)

H-Apc-D-1-Nal-D-Trp-2-Thi-Apc-NH$_2$; (SEQ ID NO: 112)

H-Apc-D-Bal-D-Trp-2-Thi-Apc-NH$_2$; (SEQ ID NO: 113)
or

H-Apc-D-1-Nal-D-Trp-Phe-Lys-NH$_2$ (SEQ ID NO: 114)

(Aib$^{2,8}$, Glu(NH-hexyl)$^{3,17}$)hGhrelin(1-28)-NH$_2$; (SEQ ID NO: 115)

(Inp$^1$, Aib$^{2,10}$, Glu(NH-hexyl)$^3$)hGhrelin(1-28)-NH$_2$; (SEQ ID NO: 116)

(1-Apc$^1$, Aib$^{2,10}$, Glu(NH-hexyl)$^3$)-hGhrelin(1-28)-NH$_2$; (SEQ ID NO: 117)

(Inp$^1$)hGhrelin(1-28)-NH$_2$; (SEQ ID NO: 118)

(Inp$^1$, Aib$^2$)hGhrelin(1-28)-NH$_2$; (SEQ ID NO: 119)

(Inp$^1$, Aib$^2$, Glu(NH-hexyl)$^3$)hGhrelin(1-28)-NH$_2$; (SEQ ID NO: 120)

(Inp$^1$, Aib$^{2,10}$)hGhrelin(1-28)-NH$_2$; (SEQ ID NO: 121)

(Inp$^1$, Aib$^{2,8}$)hGhrelin(1-28)-NH$_2$; (SEQ ID NO: 122)

(Inp$^1$, Aib$^2$, Ser(n-octanoyl)$^{17}$)hGhrelin(1-28)-NH$_2$; (SEQ ID NO: 123)

(Inp$^1$, Ser(n-octanoyl)$^{17}$)hGhrelin(1-28)-NH$_2$; (SEQ ID NO: 124)

(Asp$^3$(NH-heptyl))hGhrelin(1-28)-NH$_2$ (SEQ ID NO: 125)

(des-Ser$^2$)hGhrelin(1-28)-NH$_2$; (SEQ ID NO: 126)

(des-Gly$^1$, des-Ser$^2$)hGhrelin(1-28)-NH$_2$; (SEQ ID NO: 127)

(Aib$^1$)hGhrelin(1-28)-NH$_2$; (SEQ ID NO: 128)
and (Asp$^3$(O-hexyl))hGhrelin(1-28)-NH$_2$. (SEQ ID NO: 129)

Unless defined otherwise, all technical and scientific terms used herein have the same meaning as commonly understood by one of ordinary skill in the art to which this invention belongs. Also, all publications, patent applications, patents and other references mentioned herein are incorporated by reference.

As used herein, the expression "glucocorticoid excess" or "excess glucocorticoids" refers to patients afflicted with a condition associate with chronic exposure to above-normal levels of glucocorticoids. As a result, these patients can be characterized as having high blood levels of glucocorticoids. Examples include excessive secretion of adrenocortical hormones such as cortisol in Cushing's syndrome, or chronic exposure to glucocorticoids such as dexamethasone used as anti-inflammatory agents in many clinical scenarios such as severe respiratory distress of prematurity.

As used herein "catabolism" refers to a net breakdown of anatomical tissue. Thus a "catabolic effect" is an effect which involves a breakdown of anatomical tissues. Catabolic effects induced by excess glucocorticoids may include, but are not limited to, reduction in growth, reduction in growth rate, reduction in body weight, reduction in lean body mass, reduction in IGF-1 levels and reduction in bone mass. As used herein, a subject experiences a "reduction in growth" when the subject is shorter than the desired height, which is usually judged in relation to height and weight for similar subjects of similar ages, which is often judged in relation to height and weight charts for children and/or adults. As used herein, a subject experiences a "reduction in growth rate" when the rate of growth of the subject is slower or less than the rates for similar subjects of similar ages, which is often judged in relation to height and weight charts for children and/or adults. As used herein, "body weight" or "body mass" refers to the total weight of a subject, including both fat and lean tissues. As used herein, "body weight" or "body mass" refers to the total weight of a subject, including both fat and lean tissues. Thus, a subject experiences a reduction in body weight when the subject weighs less than similar subjects of similar ages, which is often judged in relation to height and weight charts for children and/or adults. As used herein, "lean body weight" refers to the weight of the lean tissues of a subject and excludes the weight of fat tissues of a subject. In a similar fashion to "reduced body weight", a subject experiences "reduced lean body mass" when the lean body mass of the subject is less than that of similar subjects of similar ages. As used herein, a "reduction of IGF-1" levels refers to a condition in which the circulating levels of IGF-1 in a subject are reduced as compared to similar subjects of similar ages. As used herein, a subject experiences "reduced bone mass" when the bone density of the subject is less than that of similar subjects of similar ages. A reduction in growth, reduction in growth rate, reduction in body weight, reduction in lean body mass, reduction in IGF-1 levels and reduction in bone mass may also be measured and compared to levels or values obtained in the same subject prior to the onset of the disease or condition requiring the administration of glucocorticoids.

As used herein "catabolic dysfunction" is a condition which induces a catabolic biochemical pathway in which the degradation of an anatomical structure. By "prevention of a catabolic state" we include an effect in which protein synthesis is stimulated and/or an effect in which the rate of protein degradation is decreased.

As used herein, "ameliorate" refers to the alleviation, reduction, suppression, diminishing or otherwise lessening of the catabolic effects of excess glucocorticoids.

As used herein, a "protein wasting disease" or a "protein wasting condition" is a disease or condition in which protein, i.e., lean body mass, decreases or declines or diminishes to an undesired degree and/or at an undesired rate. An example of a protein wasting disease is cachexia.

As used herein, long term administration of a medicament, such as a glucocorticoid, describes the administration of the medicament for treatment of a chronic condition. The medicament may be administered for as long as the condition exits and the patient receive benefit from the administration. Long term administration may last for several weeks, several months or even several years. In some instances, the medicament is administered for the lifetime of the patient As used herein "somatic growth" refers to growth of the body in contrast to the viscera.

As used herein "pulsatile growth hormone (or GH) secretion" refers to the rhythmical secretion of GH from the anterior pituitary gland.

As used herein "respiratory distress of prematurity" which may also be referred to as "respiratory distress syndrome" is a breathing disorder of premature newborns in which the air sacs (alveoli) in a newborn's lungs do not remain open because the production of surfactant is absent or insufficient.

As used herein "lypolysis" as used herein refers to the decomposition or splitting up of fat.

The present invention is intended to be used in all catabolic dysfunctions whether enteral or parenteral. The term "enteral" is intended to indicate that portion of the alimentary canal between the stomach and the anus. The term "parenteral" denotes that region outside of the digestive tract. The administration of ghrelin, or a functional analogue thereof, in particular [Aib$^2$, Glu$^3$(NH-hexyl)]hGhrelin(1-28)-NH$_2$ (SEQ ID NO:2), can be by both enteral and parenteral means. Enteral administration is accomplished is by using small-bore tubing placed via the nose into the gastric or duodenal regions, or through surgical implantation as in, for example, gastrostomy or jejunostomy. Parenteral routes of administration include, but are not limited to, such routes as subcutaneous, intramuscular, or intravenous injection, nasopharyngeal or mucosal absorption or transdermal absorption.

In most cases, ghrelin, or a functional analogue thereof, in particular [Aib$^2$, Glu$^3$(NH-hexyl)]hGhrelin(1-28)-NH$_2$ (SEQ ID NO:2), is administered intravenously. In intravenous administration, the therapeutically effective amount of ghrelin, or a functional analogue thereof, in particular [Aib$^2$, Glu$^3$(NH-hexyl)]hGhrelin(1-28)-NH$_2$ (SEQ ID NO:2), is in a liquid form which is administered from a reservoir directly via the placement of a needle into a large vein of the patient wherein the needle is connected to the reservoir by tubing.

As used herein, an "agonist" is a molecule which binds to the same receptor or receptors as an exemplary molecule and elicits the same or a similar response from the receptor or receptors of that exemplary molecule. For example, [Aib$^2$, Glu$^3$(NH-hexyl)]hGhrelin(1-28)-NH$_2$ (SEQ ID NO:2) is a "ghrelin agonist", that is, is a molecule which binds to the same receptor or receptors as native ghrelin and elicits the same or a similar response from binding to said receptors. The term "functional analogue" is another phrase used to describe an agonist molecule. Additional suitable ghrelin analogues include:

```
                                            (SEQ ID NO: 3)
(Dap³(octanesulfonyl))hGhrelin(1-28)-NH₂;

(SEQ ID NO: 4)
(Aib², A6c⁵)hGhrelin(1-28)-NH₂;
```

(Aib$^{2,6}$)hGhrelin(1-28)-NH$_2$; (SEQ ID NO: 5)

(Aib$^2$, 3-Pal$^9$)hGhrelin(1-28)-NH$_2$; (SEQ ID NO: 6)

(A5c$^2$)hGhrelin(1-28)-NH$_2$; (SEQ ID NO: 7)

(Act$^2$)hGhrelin(1-28)-NH$_2$; (SEQ ID NO: 8)

(Aib$^2$, Act$^6$)hGhrelin(1-28)-NH$_2$; (SEQ ID NO: 9)

(Aib$^2$, Abu$^6$)hGhrelin(1-28)-NH$_2$; (SEQ ID NO: 10)

(Aib$^2$, 4-Hyp$^7$)hGhrelin(1-28)-NH$_2$; (SEQ ID NO: 11)

(Aib$^2$, Thz$^7$)hGhrelin(1-28)-NH$_2$; (SEQ ID NO: 12)

(Aib$^2$, Pip$^7$)hGhrelin(1-28)-NH$_2$; (SEQ ID NO: 13)

(Aib$^2$, Dhp$^7$)hGhrelin(1-28)-NH$_2$; (SEQ ID NO: 14)

(Aib$^{2,8}$)hGhrelin(1-28)-NH$_2$; (SEQ ID NO: 15)

(Aib$^2$, 4-Pal$^9$)hGhrelin(1-28)-NH$_2$; (SEQ ID NO: 16)

(Aib$^2$, Taz$^9$)hGhrelin(1-28)-NH$_2$; (SEQ ID NO: 17)

(Aib$^{2,10}$)hGhrelin(1-28)-NH$_2$; (SEQ ID NO: 18)

(Aib$^2$, Tic$^7$)hGhrelin(1-28)-NH$_2$; (SEQ ID NO: 19)

(A6c$^5$)hGhrelin(1-28)-NH$_2$; (SEQ ID NO: 20)

(3-Pal$^9$)hGhrelin(1-28)-NH$_2$; (SEQ ID NO: 21)

(Aib$^8$)hGhrelin(1-28)-NH$_2$; (SEQ ID NO: 22)

(2-Thi$^9$)hGhrelin(1-28)-NH$_2$; (SEQ ID NO: 23)

(Aib$^2$, Cha$^5$)hGhrelin(1-28)-NH$_2$; (SEQ ID NO: 24)

(Aib$^2$, Glu$^3$(NH-hexyl), 4-Hyp$^7$)hGhrelin(1-28)-NH$_2$; (SEQ ID NO: 25)

((Aib$^{2,8}$, Glu$^3$(NH-hexyl))hGhrelin(1-28)-NH$_2$; (SEQ ID NO: 26)

(Aib$^2$, Glu$^3$(NH-hexyl), 3-Pal9)hGhrelin(1-28)-NH$_2$; (SEQ ID NO: 27)

(Aib$^2$, Glu$^3$(NH-hexyl), 4-Pal9)hGhrelin(1-28)-NH$_2$; (SEQ ID NO: 28)

(Aib$^2$, Glu$^3$(NH-hexyl), Taz$^9$)hGhrelin(1-28)-NH$_2$; (SEQ ID NO: 29)

(Aib$^2$, Glu$^3$(NH-hexyl), 2-Thi$^9$)hGhrelin(1-28)-NH$_2$; (SEQ ID NO: 30)

(Aib$^{2,10}$, Glu$^3$(NH-hexyl))hGhrelin(1-28)-NH$_2$; (SEQ ID NO: 31)

(Glu$^3$(NH-hexyl), 4-Hyp$^7$)hGhrelin(1-28)-NH$_2$; (SEQ ID NO: 32)

(Glu$^3$(NH-hexyl), Aib$^8$)hGhrelin(1-28)-NH$_2$; (SEQ ID NO: 33)

(Aib$^{2,12}$, Glu$^3$(NH-hexyl), 4-Pal$^9$, Orn$^{15}$)hGhrelin(1-28)-NH$_2$; (SEQ ID NO: 34)

(Glu$^3$(O-hexyl))hGhrelin(1-28)-NH$_2$; (SEQ ID NO: 35)

(Aib$^2$)hGhrelin(1-28)-NH$_2$; (SEQ ID NO: 36)

(Glu$^3$(NH-hexyl))hGhrelin(1-28)-NH$_2$; (SEQ ID NO: 37)

(Ac-Gly$^1$, Aib$^2$)hGhrelin(1-28)-NH$_2$; (SEQ ID NO: 38)

(n-butyryl-Gly$^1$)hGhrelin(1-28)-NH$_2$; (SEQ ID NO: 39)

(isobutyryl-Gly$^1$)hGhrelin(1-28)-NH$_2$; (SEQ ID NO: 40)

(n-octanoyl-Gly$^1$)hGhrelin(1-28)-NH$_2$; (SEQ ID NO: 41)

Cys$^3$(S(CH$_2$)$_9$CH$_3$)hGhrelin(1-28)-NH$_2$; (SEQ ID NO: 42)

(Lys$^5$)hGhrelin(1-28)-NH$_2$ (SEQ ID NO: 43)

Inp-D-2-Nal-D-Trp-Phe-Lys-NH$_2$ (SEQ ID NO: 44)

H-Inp-D-1-Nal-D-Trp-3-Pal-Lys-NH$_2$; (SEQ ID NO: 45)

H-Inp-D-2-Nal-D-Trp-Orn-Lys-NH$_2$; (SEQ ID NO: 46)

H-Inp-D-Bip-D-Trp-Phe-Lys-NH$_2$; (SEQ ID NO: 47)

H-Inp-D-2-Nal-D-Trp-Pff-Lys-NH$_2$; (SEQ ID NO: 48)

H-Inp-D-2-Nal-D-Trp-2-Thi-Lys-NH$_2$; (SEQ ID NO: 49)

H-Inp-D-2-Nal-D-Trp-Taz-Lys-NH$_2$; (SEQ ID NO: 50)

H-Inp-D-Dip-D-Trp-Phe-Lys-NH$_2$; (SEQ ID NO: 51)

H-Inp-D-Bpa-D-Trp-Phe-Lys-NH$_2$; (SEQ ID NO: 52)

H-Inp-D-2-Nal-D-Bpa-Phe-Lys-NH$_2$; (SEQ ID NO: 53)

H-Inp-D-2-Nal-D-Trp-3-Pal-NH$_2$; (SEQ ID NO: 54)

H-Inp-D-2-Nal-D-Trp-4-Pal-NH$_2$; (SEQ ID NO: 55)

H-Inp-D-1-Nal-D-Trp-3-Pal-NH$_2$; (SEQ ID NO: 56)

H-Inp-D-Bip-D-Trp-Phe-NH$_2$; (SEQ ID NO: 57)

H-Inp-D-2-Nal-D-Trp-Thr(Bzl)-NH$_2$; (SEQ ID NO: 58)

H-Inp-D-2-Nal-D-Trp-Pff-NH₂; (SEQ ID NO: 59)

H-Inp-D-2-Nal-D-Trp-2-Thi-NH₂; (SEQ ID NO: 60)

H-Inp-D-2-Nal-D-Trp-Taz-NH₂; (SEQ ID NO: 61)

H-Inp-D-Dip-D-Trp-Phe-NH₂; (SEQ ID NO: 61)

H-Inp-D-Dip-D-Trp-Phe-NH₂; (SEQ ID NO: 62)

H-Inp-D-2-Nal-D-Dip-Phe-NH₂; (SEQ ID NO: 63)

H-Inp-D-Bal-D-Trp-Phe-NH₂; (SEQ ID NO: 64)

H-Inp-D-2-Nal-D-Bal-Phe-NH₂; (SEQ ID NO: 65)

H-Inp-D-2-Nal-D-Trp-3-Pal-Lys-NH₂; (SEQ ID NO: 66)

H-Inp-D-Trp-D-2-Nal(Ψ)-Pim; (SEQ ID NO: 67)

H-Inp-D-Bal-D-Trp-2-Thi-Lys-NH₂; (SEQ ID NO: 68)

H-Inp-D-Bal-D-Trp-Phe-Lys-NH₂; (SEQ ID NO: 69)

H-Inp-D-1-Nal-D-Trp-2-Thi-Lys-NH₂; (SEQ ID NO: 70)

H-Inp-D-2-Nal-D-Trp-Phe-Apc-NH₂; (SEQ ID NO: 71)

H-Inp-D-1-Nal-D-Trp-Phe-Apc-NH₂; (SEQ ID NO: 72)

H-Inp-D-Bal-D-Trp-Phe-Apc-NH₂; (SEQ ID NO: 73)

H-Apc-D-2-Nal-D-Trp-Phe-Lys-NH₂; (SEQ ID NO: 74)

H-Apc-D-1-Nal-D-Trp-2-Thi-Lys-NH₂; (SEQ ID NO: 75)

H-Inp-D-1-Nal-D-Trp-2-Thi-NH₂; (SEQ ID NO: 76)

H-Apc-D-1-Nal-D-Trp-Phe-NH₂; (SEQ ID NO: 77)

H-Inp-D-2-Nal-D-Trp(Ψ)-Pim; (SEQ ID NO: 78)

H-Inp-D-1-Nal-D-Trp(Ψ)-Pim; (SEQ ID NO: 79)

H-Inp-D-Bal-D-Trp(Ψ)-Pim; (SEQ ID NO: 80)

H-Aib-D-Ser(Bzl)-D-Trp(Ψ)-Pim; (SEQ ID NO: 81)

H-Inp-D-1-Nal-D-Trp-Taz-Lys-NH₂; (SEQ ID NO: 82)

H-Inp-D-Bal-D-Trp-Taz-Lyz-NH₂; (SEQ ID NO: 83)

H-Apc-D-1-Nal-D-Trp-Taz-Lys-NH₂; (SEQ ID NO: 84)

H-Apc-D-Bal-D-Trp-Taz-Lys-NH₂; (SEQ ID NO: 85)

H-Apc-D-Bal-D-Trp-2-Thi-Lys-NH₂; (SEQ ID NO: 86)

H-Apc-D-Bal-D-Trp-Phe-Lys-NH₂; (SEQ ID NO: 87)

H-Apc-D-1-Nal-D-Trp-Phe-Apc-NH₂; (SEQ ID NO: 88)

H-Apc-D-Bal-D-Trp-Phe-Apc-NH₂; (SEQ ID NO: 89)

H-Apc-D-1-Nal-D-1-Nal-Phe-Apc-NH₂; (SEQ ID NO: 90)

H-Apc-D-1-Nal-D-2-Nal-Phe-Apc-NH₂; (SEQ ID NO: 91)

H-Apc-D-1-Nal-D-1-Nal-Phe-Lys-NH₂; (SEQ ID NO: 92)

H-Apc-D-Bal-D-1-Nal-Phe-Apc-NH₂; (SEQ ID NO: 93)

H-Apc-D-Bal-D-2-Nal-Phe-Apc-NH₂; (SEQ ID NO: 94)

H-Apc-D-Bal-D-2-Nal-Phe-Lys-NH₂; (SEQ ID NO: 95)

H-Apc-D-1-Nal-D-Trp-2-Thi-NH₂; (SEQ ID NO: 96)

H-Apc-D-Bal-D-Trp-Phe-NH₂; (SEQ ID NO: 97)

H-Apc-D-1-Nal-D-Trp-Taz-NH₂; (SEQ ID NO: 98)

H-Apc-D-Bal-D-Trp-2-Thi-NH₂; (SEQ ID NO: 99)

H-Apc-D-Bal-D-Trp-Taz-NH₂; (SEQ ID NO: 100)

H-Apc-D-2-Nal-D-Trp-2-Thi-NH₂; (SEQ ID NO: 101)

H-Apc-D-2-Nal-D-Trp-Taz-NH₂; (SEQ ID NO: 102)

H-Inp-D-1-Nal-D-Trp-Taz-Apc-NH₂; (SEQ ID NO: 103)

H-Inp-D-Bal-D-Trp-Taz-Apc-NH₂; (SEQ ID NO: 104)

H-Apc-D-1-Nal-D-Trp-Taz-Apc-NH₂; (SEQ ID NO: 105)

H-Apc-D-Bal-D-Trp-Taz-Apc-NH₂; (SEQ ID NO: 106)

H-Inp-D-2-Nal-D-Trp-4-Pal-Lys-NH₂; (SEQ ID NO: 107)

H-Inp-D-2-Nal-D-Trp-Thr(Bzl)-Lys-NH₂; (SEQ ID NO: 108)

H-Apc-D-Bal-D-1-Nal-Phe-Lys-NH₂; (SEQ ID NO: 109)

H-Inp-D-1-Nal-D-Trp-2-Thi-Apc-NH₂; (SEQ ID NO: 110)

H-Inp-D-Bal-D-Trp-2-Thi-Apc-NH₂; (SEQ ID NO: 111)

```
H-Apc-D-1-Nal-D-Trp-2-Thi-Apc-NH₂;                              (SEQ ID NO: 112)

H-Apc-D-Bal-D-Trp-2-Thi-Apc-NH₂;                                (SEQ ID NO: 113)
or

H-Apc-D-1-Nal-D-Trp-Phe-Lys-NH₂                                 (SEQ ID NO: 114)

(Aib²,⁸, Glu(NH-hexyl)³,¹⁷)hGhrelin(1-28)-NH₂;                  (SEQ ID NO: 115)

(Inp¹, Aib²,¹⁰, Glu(NH-hexyl)³)hGhrelin(1-28)-NH₂;              (SEQ ID NO: 116)

(1-Apc¹, Aib²,¹⁰, Glu(NH-hexyl)³)-                              (SEQ ID NO: 117)
hGhrelin(1-28)-NH₂;

(Inp¹)hGhrelin(1-28)-NH₂;                                       (SEQ ID NO: 118)

(Inp¹, Aib²)hGhrelin(1-28)-NH₂;                                 (SEQ ID NO: 119)

(Inp¹, Aib², Glu(NH-hexyl)³)hGhrelin(1-28)-NH₂;                 (SEQ ID NO: 120)

(Inp¹, Aib²,¹⁰)hGhrelin(1-28)-NH₂;                              (SEQ ID NO: 121)

(Inp¹, Aib²,⁸)hGhrelin(1-28)-NH₂;                               (SEQ ID NO: 122)

(Inp¹, Aib², Ser(n-octanoyl)¹⁷)hGhrelin(1-28)-NH₂;              (SEQ ID NO: 123)

(Inp¹, Ser(n-octanoyl)¹⁷)hGhrelin(1-28)-NH₂;                    (SEQ ID NO: 124)

(Asp³(NH-heptyl))hGhrelin(1-28)-NH₂                             (SEQ ID NO: 125)

(des-Ser²)hGhrelin(1-28)-NH₂;                                   (SEQ ID NO: 126)

(des-Gly¹, des-Ser²)hGhrelin(1-28)-NH₂;                         (SEQ ID NO: 127)

(Aib¹)hGhrelin(1-28)-NH₂;                                       (SEQ ID NO: 128)
and (Asp³(O-hexyl))hGhrelin(1-28)-NH₂.                              (SEQ ID NO: 129)
```

The term "substantially associated with" as applied to the catabolic dysfunctions for which the method of the invention is effective.

Functional analogues of ghrelin which retain the characteristics of ghrelin are contemplated as equivalents.

As used herein a "therapeutically effective amount" for the administration of ghrelin, or a functional analogue thereof, in particular [Aib², Glu³(NH-hexyl)]hGhrelin(1-28)-NH₂ (SEQ ID NO:2), are those amounts large enough to prevent the catabolism or atrophy of the tissues of the body in order to maintain metabolic homeostasis.

As used herein "therapeutic composition" or "pharmaceutical composition" is defined as comprising of ghrelin, or a functional analogue thereof, in particular [Aib², Glu³(NH-hexyl)]hGhrelin(1-28)-NH₂ (SEQ ID NO:2), which may also contain excipients such as water, minerals and other compatible carriers.

The use of ghrelin, or a functional analogue (agonist) thereof, in particular [Aib², Glu³(NH-hexyl)]hGhrelin(1-28)-NH₂ (SEQ ID NO:2), by the method according to the invention is ideally suited for the preparation of compositions. These compositions may comprise ghrelin, or a functional analogue thereof, in particular [Aib², Glu³(NH-hexyl)]hGhrelin(1-28)-NH₂ (SEQ ID NO:2), alone or in combination with other chemicals. Ghrelin analogues taught, discussed and disclosed in the following patent publications may be used to practice the claimed methods:

PCT Patent Publication WO 04/009616;

PCT Patent Publication WO 04/014415;

U.S. Provisional Patent Application Ser. No. 60/721,557;

U.S. Provisional Patent Application Ser. No. 60/721,916;

U.S. Provisional Patent Application Ser. No. 60/748,904; and

U.S. Provisional Patent Application Ser. No. 60/750,771.

Ghrelin analogs may be administered in any suitable dosage form, e.g., formulated with any known organic or inorganic pharmaceutical carrier. Carriers so utilized should be inert (non-reactive). Preferably for enteral administration, for example, in tablets, capsules or the like, conventional carriers, e.g., gelatin, lactose, starches or the like may be incorporated therein. If desired, the preparations may be sterilized or may additionally contain known auxiliary substances, such as preserving, stabilizing, wetting or emulsifying agents, salts for regulating osmotic pressure, buffers, extenders and/or other conventional carriers and the like. The content of active substances in these preparations, such as an ampoule or a tablet, may be within the range of from about 5 to 100 milligrams, preferably from about 5 to 10 milligrams. Preparations for parenteral administration include sterile aqueous or non-aqueous solutions, suspensions, and emulsions. Carriers or occlusive dressings can be used to increase skin permeability and enhance absorption. Containers containing the composition of the invention can be used to facilitate the administration of ghrelin, or a functional analogue thereof, in particular [Aib², Glu³(NH-hexyl)]hGhrelin(1-28)-NH₂ (SEQ ID NO:2), according to the method of the invention. These containers are designed to contain, for example, the daily dosage of ghrelin, or a functional analogue thereof, in particular [Aib², Glu³(NH-hexyl)]hGhrelin(1-28)-NH₂ (SEQ ID NO:2), to be administered to the patient.

Nomenclature and Abbreviations
Certain amino acids present in compounds of the invention can be and are represented herein as follows:

| Symbol | Meaning |
| --- | --- |
| Abu | α-aminobutyric acid |
| Acc | 1-amino-1-cyclo($C_3$—$C_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |

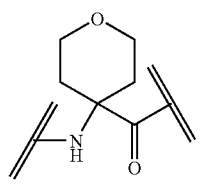

| | |
| --- | --- |
| Act | denotes the structure |
| Aib | α-aminoisobutyric acid |
| Aic | 2-aminoindan-2-carboxylic acid |
| Ala or A | alanine |
| β-Ala | beta-alanine |

Nomenclature and Abbreviations
Certain amino acids present in compounds of the invention can be and are represented herein as follows:

| Symbol | Meaning |
|---|---|
| | 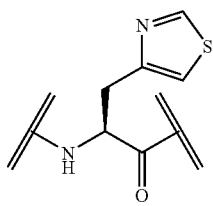 |
| Apc | denotes the structure: |
| Arg or R | arginine |
| hArg | homoarginine |
| Asn or N | asparagine |
| Asp or D | aspartic acid |
| Ava | 5-amino-n-valeric acid |
| Cha | β-cyclohexylalanine |
| Cys or C | cysteine |
| hCys | L-homocysteine |
| Dab | 2,4-diaminobutyric acid |
| Dap | 2,3-diaminopropionic acid |
| Dhp | 3,4-dehydroproline |
| Dmt | 5,5-dimethylthiazolidine-4-carboxylic acid |
| 2-Fua | β-(2-furyl)-alanine |
| Gln or Q | glutamine |
| Glu or E | glutamic acid |
| Gly or G | glycine |
| His or H | histidine |
| 3-Hyp | trans-3-hydroxy-L-proline, i.e., (2S,3S)-3-hydroxypyrrolidine-2-carboxylic acid |
| 4-Hyp | 4-hydroxyproline, i.e., (2S,4R)-4-hydroxypyrrolidine-2-carboxylic acid |
| Ile or I | isoleucine |
| Inc | indoline-2-carboxylic acid |
| Inp | isonipecotic acid |
| Ktp | 4-ketoproline |
| Leu or L | leucine |
| hLeu | homoleucine |
| Lys or K | lysine |
| Met or M | methionine |
| 1-Nal | β-(1-naphthyl)-L-alanine |
| 2-Nal | β-(2-naphthyl)-L-alanine |
| Nle | norleucine |
| Nva | norvaline |
| Oic | octahydroindole-2-carboxylic acid |
| Orn | ornithine |
| 2-Pal | β-(2-pyridyl)alanine |
| 3-Pal | β-(3-pyridyl)alanine |
| 4-Pal | β-(4-pyridyl)alanine |
| Phe or F | phenylalanine |
| hPhe | homophenylalanine |
| Pip | pipecolic acid |
| Pro or P | proline |
| Ser or S | serine |
| | 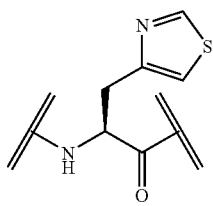 |
| Taz | β-(4-thiazolyl)alanine, i.e., |
| 2-Thi | β-(2-thienyl)alanine |
| 3-Thi | β-(3-thienyl)alanine |
| Thp | 4-amino-4-carboxytetrahydropyran |
| Thr or T | threonine |
| Thz | thiazolidine-4-carboxylic acid |
| Tic | 1,2,3,4-tetrahydroisoquinoline-3-carboxylic acid |
| Tle | tert-leucine |

Nomenclature and Abbreviations
Certain amino acids present in compounds of the invention can be and are represented herein as follows:

| Symbol | Meaning |
|---|---|
| Trp or W | tryptophan |
| Tyr or Y | tyrosine |
| Val or V | valine |

Where the amino acid has isomeric forms, it is the L form of the amino acid that is represented unless otherwise explicitly indicated.

Certain other abbreviations used herein are defined as follows:
Boc: tert-butyloxycarbonyl
BSA: bovine serum albumin
Bzl: benzyl
DCM: dichloromethane
DIC: N,N-diisopropylcarbodiimide
DIEA: diisopropylethyl amine
Dmab: 4-{N-(1-(4,4-dimethyl-2,6-dioxocyclohexylidene)-3-methylbutyl)-amino} benzyl
DMAP: 4-(dimethylamino)pyridine
DMF: dimethylformamide
DNP: 2,4-dinitrophenyl
EDTA ethylenediaminetetracetic acid
Fmoc: fluorenylmethyloxycarbonyl
HBTU: 2-(1H-benzotriazole-1-yl)-1,1,3,3-tetramethyluronium hexafluorophosphate
cHex cyclohexyl
HOAT: O-(7-azabenzotriazol-1-yl)-1,1,3,3-tetramethyluronium hexafluorophosphate
HOBt: 1-hydroxy-benzotriazole
MBHA 4-methylbenzhydrylamine
Mmt: 4-methoxytrityl
NMP: N-methylpyrrolidone
Pbf: 2,2,4,6,7-pentamethyldihydrobenzofuran-5-sulfonyl
PhiPr γ-2-phenylisopropyl ester
tBu: tert-butyl
TIS: triisopropylsilane
TOS: tosyl
trt trityl
TFA: trifluoro acetic acid
TFFH: tetramethylfluoroforamidinium hexafluorophosphate
Z: benzyloxycarbonyl The nomenclature used to define the peptides is that typically used in the art wherein the amino group at the N-terminus appears to the left and the carboxyl group at the C-terminus appears to the right, i.e., stand for the structure of —NH—C(R)(R')—CO— wherein R and R' each is, independently, hydrogen or the side chain of an amino acid (e.g., R=CH₃ and R'=H for Ala), or R' and R' may be joined to form a ring system. For the N-terminal amino acid, the abbreviation stands for the structure of:

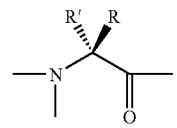

or when the N-terminal amino acid is isonipecotic acid (Inp), the abbreviation stands for the structure of:

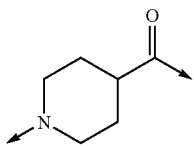

A peptide of this invention is also denoted herein by another format, e.g., (Aib$^2$)hGhrelin(1-28)-NH$_2$, with the substituted amino acid(s) from the natural sequence placed between the first set of parentheses (e.g., Aib$^2$ for Ser$^2$ in hGhrelin). The numbers between the second set of parentheses refer to the number of amino acids present in the peptide (e.g., hGhrelin(1-18) refers to amino acids 1 through 18 of the peptide sequence for human Ghrelin). The designation "NH$_2$" in e.g., (Aib$^2$)hGhrelin(1-28)-NH$_2$, indicates that the C-terminus of the peptide is amidated. (Aib$^2$)hGhrelin(1-28), or, alternatively, (Aib$^2$)hGhrelin(1-28)-OH indicates that the C-terminus is the free acid.

Unless otherwise stated, those amino acids with a chiral center are provided in the L-enantiomer. Reference to "a derivative thereof" refers to a modified amino acid such as the corresponding D-amino acid, a N-alkyl-amino acid, a β-amino acid, or a labeled amino acid.

"Acyl" refers to R"—C(O)—, where R" is H, alkyl, substituted alkyl, heteroalkyl, substituted heteroalkyl, alkenyl, substituted alkenyl, aryl, alkylaryl or substituted alklyaryl.

"Alkyl" refers to a hydrocarbon group containing one or more carbon atoms where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Examples of alkyl acids containing, or consisting of —(CH$_2$)$_{0-20}$—COOH include 2-norbornane acetic acid, tert-butyric acid and 3-cyclopentyl propionic acid.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present.

"Aryl" refers to an optionally substituted aromatic group with at least one ring having a conjugated π-electron system containing up to two conjugated or fused ring systems. Aryl includes carbocyclic aryl, heterocyclic aryl and biaryl groups. Preferably, the aryl is a 5- or 6-membered ring. Preferred atoms for a heterocyclic aryl are one or more sulfurs, oxygens and/or nitrogens. Examples of aryl include phenyl, 1-naphthyl, 2-naphthyl, indole, quinoline, 2-imidazole and 9-anthracene. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with 1 to 5 halogens, —CF$_3$, —OCF$_3$ and —(CH$_2$)$_{0-20}$—COOH. In different embodiments, the aryl contains 0, 1, 2, 3 or 4 substituents.

The term "halo" encompasses fluoro, chloro, bromo and iodo.

The term "(C$_1$-C$_{12}$)hydrocarbon moiety" encompasses alkyl, alkenyl and alkynyl and, in the case of alkenyl and alkynyl, there are C$_2$-C$_{12}$.

"Alkylaryl" refers to an "alkyl" joined to an "aryl".

What is meant by Glu(O-hexyl) is

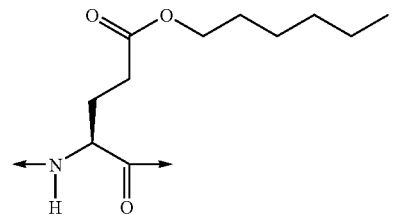

What is meant by Asp(1-heptanol) is

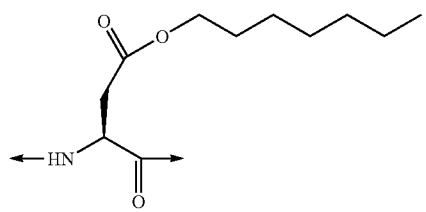

What is meant by Glu(NH-hexyl) is

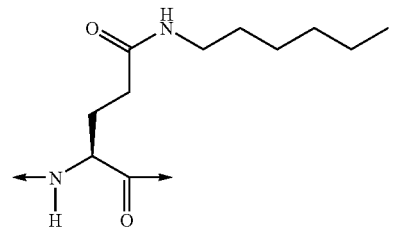

What is meant by Ser(n-octanoyl) or Ser(C(O)-heptyl) is
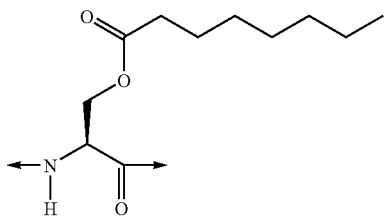
What is meant by Dap(1-octanesulfonyl) is
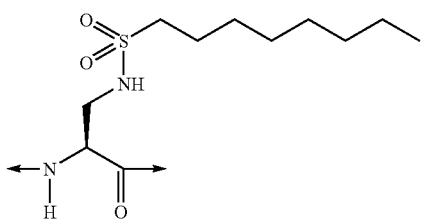
What is meant by Cys(R$^{15}$) is:
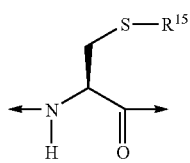
What is meant by Cys(S-heptyl) is
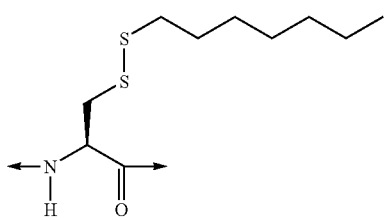
What is meant by Dap(octanoyl) is
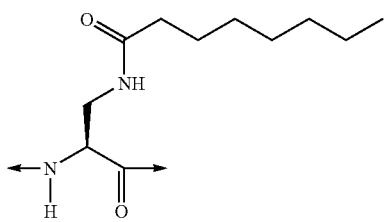
What is meant by biotinyl is
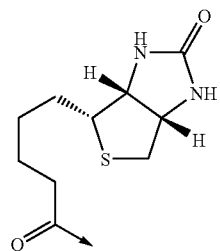
What is meant by myristyl is
What is meant by Lys(biotinyl) is
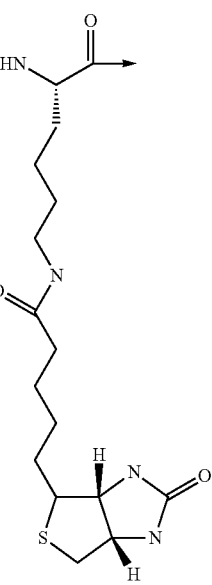

What is meant by Lys(myristyl) is

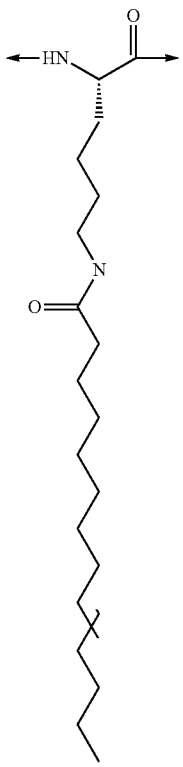

The present invention includes diastereomers as well as their racemic and resolved enantiomerically pure forms. Ghrelin analogs can contain D-amino acids, L-amino acids or a combination thereof. Preferably, amino acids present in a ghrelin analog are the L-enantiomers.

Preferred derivatives of analogs of the invention comprise D-amino acids, N-alkyl-amino acids, β-amino acids and/or one or more labeled amino acids (including a labeled version of a D-amino acid, an N-alkyl-amino acid, or a β-amino acid). A labeled derivative indicates the alteration of an amino acid or amino acid derivative with a detectable label. Examples of detectable labels include luminescent, enzymatic and radioactive labels. Both the type of label and the position of the label can affect analog activity. Labels should be selected and positioned so as not to substantially alter the activity of the ghrelin analog at the GHS receptor. The effect of a particular label and position on ghrelin activity can be determined using assays measuring ghrelin activity and/or binding.

A protecting group covalently joined to the C-terminal carboxyl group reduces the reactivity of the carboxyl terminus under in vivo conditions. The carboxyl terminus protecting group is preferably attached to the α-carbonyl group of the last amino acid. Preferred carboxyl terminus protecting groups include amide, methylamide, and ethylamide.

EXAMPLES

The above disclosure generally describes the present invention. A more complete understanding can be obtained by reference to the following specific examples which are provided herein for purposes of illustration only and are not intended to be limiting unless otherwise specified.

The ghrelin analogues of the invention can be produced using the techniques discussed herein to produce the preferred embodiment, [Aib$^2$, Glu$^3$(NH-hexyl)]hGhrelin(1-28)-NH$_2$ (SEQ ID NO:2), as well as techniques that are well known in the art. For example, a polypeptide region of a ghrelin analog can be chemically or biochemically synthesized and modified. Techniques for chemical synthesis of polypeptides are also well known in the art (Vincent in *Peptide and Protein Drug Delivery*, New York, N.Y., Dekker, 1990). For example, the peptides of this invention can be prepared by standard solid phase peptide synthesis (Stewart, J. M., et al., Solid Phase Synthesis (Pierce Chemical Co., 2d ed. 1984)).

Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989.

Example 1

Synthesis of Ghrelin Analogs

The preferred embodiment [Aib$^2$, Glu$^3$(NH-hexyl)]hGhrelin(1-28)-NH$_2$ (SEQ ID NO:2), was synthesized on an Applied Biosystems® (Foster City, Calif.) model 430A® peptide synthesizer which was modified to do accelerated Boc-chemistry solid phase peptide synthesis (Schnolzer, et al., Int. J. Peptide Protein Res., 1992, 40:180). A 4-methylbenzhydrylamine (hereinafter referred to as "MBHA") resin (Peninsula, Belmont, Calif.) with the substitution of 0.91 mmol/g was used. The Boc amino acids (Midwest BioTech®, Fishers, Ind.; Novabiochem®, San Diego, Calif.) were used with the following side chain protection: Boc-Ala-OH, Boc-Arg(Tos)-OH, Boc-His(DNP)-OH, Boc-Val-OH, Boc-Leu-OH, Boc-Gly-OH, Boc-Gln-OH, Boc-Lys(2ClZ)-OH, Boc-Ser(Bzl)-OH, Boc-Phe-OH, Boc-Glu(OcHex)-OH and Boc-Pro-OH. With respect to the substituted positions, Boc-Gly-OH was used as the residue at position 1, Fmoc-Aib-OH was used as the residue at position 2, and Fmoc-Glu(OtBu)-OH (Novabiochem®, San Diego, Calif.) was used for the residue at position 3 in the sequence. The synthesis was carried out on a 0.25 mmol scale. The Boc groups were removed by treatment with 100% TFA for 2×1 minute Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 minutes.

At the end of the assembly of the first 25 residues on the ABI 430A® peptide synthesizer and before the coupling of Fmoc-Glu(OtBu)-OH, the protected peptide-resin was transferred into a reaction vessel on a shaker for manual synthesis. After removing the Boc protecting group by using 100% TFA for 2×1 minute and washing with DMF, the resin was mixed with Fmoc-Glu(OtBu)-OH (2.5 mmol) which was pre-activated with HBTU (2.0 mmol), HOBt (2.0 mmol) and DIEA (1.0 mL) in 4 mL of DMF. The mixture was shaken for 2 hours. This coupling step was repeated. After washing with DMF, the resin was treated with a TFA solution containing 5% water and 5% TIS for 2 hours to remove the tBu protecting group in the side chain of the Glu residue. The resin was neutralized with 10% DIEA in DMF and washed with DMF and DCM and then treated with hexylamine (2.0 mmol), DIC (2.0 mmol), HOBT (2.0 mmol) in 5 ml of DCM for 2×2 hours. The resin was washed with DMF and treated with 25% piperidine in DMF for 30 minutes to remove the Fmoc protecting groups. After washing with DMF and DCM, the resin was transferred into the reaction vessel on the ABI 430A® peptide synthesizer for the assembly of the rest two residues.

At the end of the assembly of the whole peptide chain, the resin was treated with a solution of 20% mercaptoethanol/10% DIEA in DMF for 2×30 minutes to remove the DNP group on the histidine side chain. The N-terminal Boc group was then removed by treatment with 100% TFA for 2×2 minutes. The peptide-resin was washed with DMF and DCM and dried under reduced pressure. The final cleavage was done by stirring the peptide-resin in 10 mL of HF containing 1 mL of anisole and dithiothreitol (50 mg) at 0° C. for 75 minutes. HF was removed by a flow of nitrogen. The residue was washed with ether (6×10 mL) and extracted with 4N HOAc (6×10 mL).

This crude product was purified on a reverse-phase preparative HPLC using a column (4×43 cm) of $C_{18}$ DYNAMAX-100A°® (Varian®, Walnut Creek, Calif.). The column was eluted with a linear gradient from 75% A and 25% B to 55% A and 45% B at flow rate of 10 mL/minute for an hour where A was 0.1% TFA in water and B was 0.1% TFA in acetonitrile. Fractions were collected and checked on an analytical HPLC. Those containing pure product were combined and lyophilized to dryness. 31.8 mg of a white solid were obtained.

Purity was 97% based on analytical HPLC analysis. Electro-spray ionization mass spectrometry (ESI MS) analysis gave the molecular weight at 3366.95 (in agreement with the calculated molecular weight of 3367.24).

Example 2

In Vitro Studies

Phosphoinositide Turnover

CHO-K1 cells, expressing the human recombinant GHS-1a receptor were harvested and resuspended in a phosphate-buffered saline solution containing 25 mM glucose and 75 mM sucrose (PBS+GS) and pre-incubated with 25 µCi/ml myo[$^3$H]inositol for 60 min/37° C. The cells were washed, resuspended in PBS+GS, and incubated with LiCl (100 mM) and GHS peptides in a final volume of 0.30 ml. The reaction was terminated by the addition of chloroform/methanol (1:2) and the total [$^3$H]inositol phosphates were isolated as previously described (Snider et al. *J. Neurochem.* 1986, 47:1214-1218; see also FIG. 1).

Example 3

In Vivo Studies

3A) Dose-related effects of [Aib$^2$, Glu$^3$(NH-hexyl)]hGhrelin (1-28)-NH$_2$ (SEQ ID NO:2) on GH secretion in freely moving rats During the study, the animals were maintained in accordance with the guidelines of the Italian Ministry of Health for the care and use of laboratory animals (*Decreto legge* 116/92). Young male Sprague-Dawley rats (*Rattus norvegicus*) were used in this study. Animals were obtained from Harlan, Italy (S. Pietro al Natisone, Italy) and were kept in a temperature-controlled environment (21-23° C.) under 12:12 hour light:dark exposure continuous period wherein light exposure began at 0800 and ended at 2000 h. Animals were provided ad libitum water and food consisting of standard pellet chow (Piccioni, Gessate-Milano, Italy) containing at least 3% fat, 56% carbohydrate and 19% protein. The total calorie content was approximately 3200 calories/kg of pellets.

Figure 2:
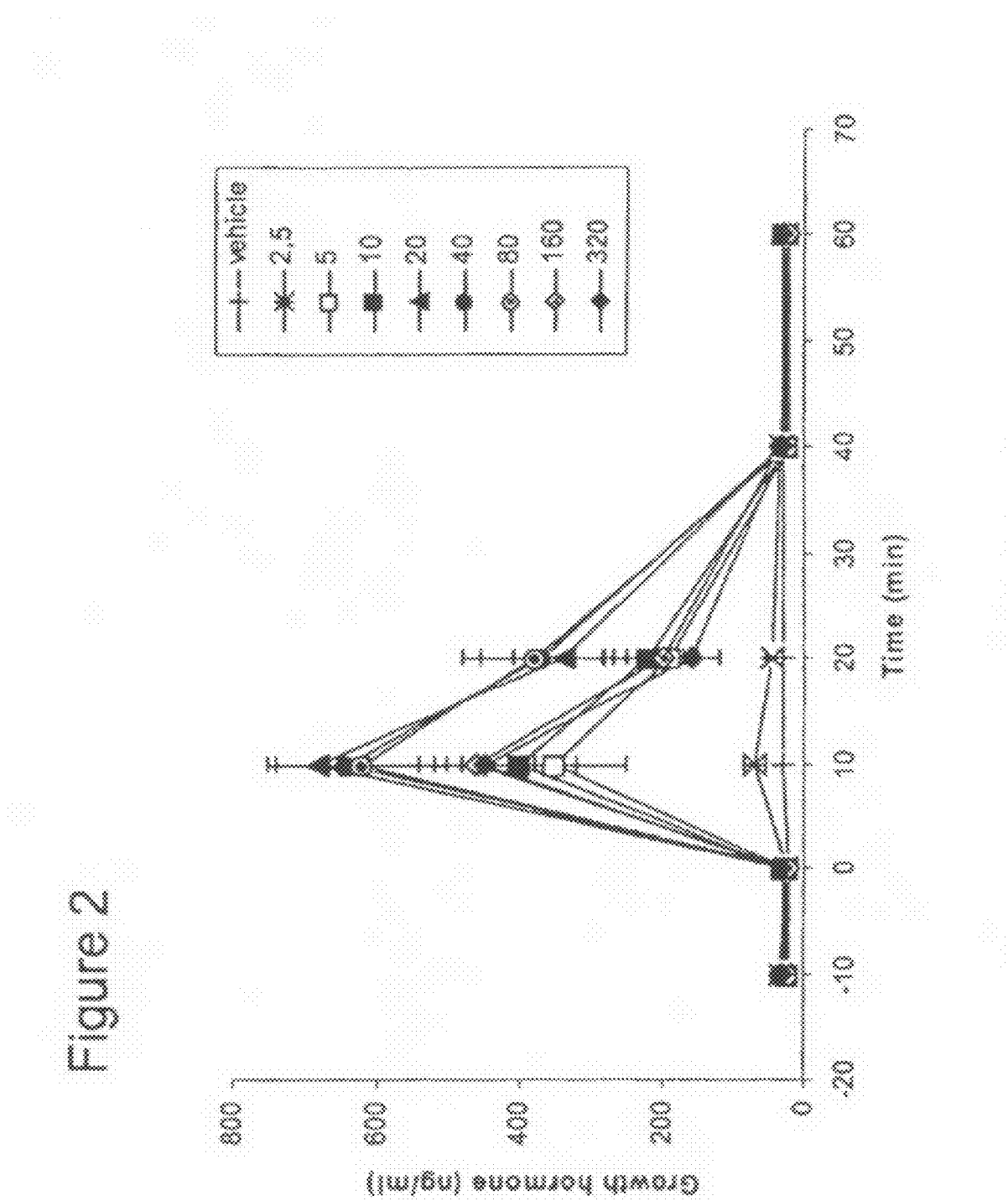
FIG. 2. Dose-response effect of intravenous administration of [Aib$^2$, Glu$^3$(NH-hexyl)]hGhrelin(1-28)-NH$_2$ (SEQ ID NO:2) (indicated as "A") on GH secretion in freely moving rats. Dose values are expressed as nmole/kg. Each experimental point represents the mean±SEM of four replicate animals. When no error bars are illustrated, the SEM is smaller than the height occupied by the symbol representing the mean.

Rats (200-250 g) were anesthetized with chlorohydrate (500 mg/kg) and fit with a jugular-right atrial cannula at least 18 hours prior to the experiment. To determine basal hormone levels, blood samples were withdrawn into heparinized syringes at —10 and 0 minutes from fully conscious, freely-moving rats. Immediately following the 0 minute blood sample, the rats were injected with either [Aib$^2$, Glu$^3$(NH-hexyl)]hGhrelin(1-28)-NH$_2$ (SEQ ID NO:2) or vehicle (a sterile saline solution with 0.25% (w/v) bovine serum albu-min) via the indwelling cannula. Subsequent blood samples were withdrawn approximately 10, 20, 40 and 60 minutes after the initial injection. Plasma was separated and stored until assay for GH (see FIG. 2).

3B) Effects of Various Pharmacological Treatments on Growth Parameters 3B.1) Animal Care and Operative Procedure Thirty-two prepubertal male Sprague-Dawley rats approximately 21 days old and weighing between 45 and 55 grams, were obtained from Harlan, Italy (S. Pietro al Natisone, ITALY). During the study, the animals were maintained in accordance with the guidelines of the Italian Ministry of Health for the care and use of laboratory animals (*Decreto legge* 116/92). The animals were randomly divided into two treatment groups and kept in a controlled environment at a constant temperature of 21-23° C. with 12:12 light/dark exposure continuous period wherein the light exposure began at approximately 8:00 am and ended at approximately 8:00 pm. The animals were provided with water and food ad libitum consisting of an approximate 3200 calories/kg daily diet of standard pellet chow provided by Piccioni, Gessate-Milano, Italy (containing at least 19% protein, 3% fat and 56% carbohydrate).

Beginning on the 23$^{rd}$ day (i.e., the animals were 23 days old), 16 of the study animals were treated intraperitoneally (Ip) daily with 40 µg/kg of either saline or dexamethasone sodium phosphate (sold under the trademark Decadron® by Merck Pharmaceuticals, West Point, Pa.). Beginning on the 30$^{th}$ day (i.e., the animals were 30 days old), the subgroup of 16 studied animals was further divided into groups of 8 and treated subcutaneously three times daily (at approximately 9:00 am, 1:00 pm and 5:00 pm) with either 80 nmoles/kg of the preferred ghrelin analog [Aib$^2$, Glu$^3$(NH-hexyl)]hGhrelin(1-28)-NH$_2$ (SEQ ID NO:2) (IPSEN, Milford, Mass.) dissolved in a sterile saline solution with 0.25% bovine serum albumin or vehicle (the saline-bovine serum albumin solution alone). This regimen continued for 24 days during which time the studied animals were weighed two times per week. At irregular intervals, the cumulative food intake for a 24-hour period of time was measured. Beginning on the 46$^{th}$ day (i.e., the animals were 46 days old), the length of the test and control animals from nose to anus was measured (hereinafter referred to as "the nose-anal length"). On the 47$^{th}$ day (i.e., the animals were 47 days old), all food was denied to the test subjects commencing at 8:00 am. Small samples of blood were taken via percutaneous puncture of the tail to assess blood glucose levels during the treatment period.

The test animals received two subcutaneous administrations of [Aib$^2$, Glu$^3$(NH-hexyl)]hGhrelin(1-28)-NH$_2$ (SEQ ID NO:2) at approximately 9:00 am and 1:00 pm. The studied animals were sacrificed by rapid decapitation at approximately 2:00 pm, trunk blood collected for hormone level determinations, and the epididymal fat pads removed and weighed.

3B.2) Preparation and Analysis of Samples

Samples of trunk blood were taken from the test subjects following decapitation. The blood samples were collected in tubes containing EDTA, separated by centrifugation, and stored at −20° C. Plasma insulin, IGF-1, and corticosterone levels were all measured using commercial RIA kits (Insulin and Corticosterone kits were both obtained from ICN-Biomedicals, Asse-Relegem, BELGIUM and the rIGF-1 test kit was obtained from Mediagnostic GMbH, Tubingen, GERMANY). Glucose concentration was determined using the Glucotrend® Soft Test System blood glucose meter (Roche Diagnostics, Barcelona, SPAIN).

3B.3) Calculations and Statistical Analysis

Unless otherwise stated, the results reported in FIGS. 3-6 are expressed as the mean±SEM of eight replicate test subjects. Data was analyzed for statistical significance by one-way ANOVA which determines the variation (variance) within the groups and how that variation translates into variation (i.e. differences) between the groups, taking into account how many subjects there are in each group. This statistical analysis was followed by Dunnett's t test or Tukey's test for multiple comparisons used to determine whether the means of the control groups differed significantly. The linear correlation analysis was performed either by Pearson's parametric test or by Spearman's nonparametric test. A P value below 0.05 was considered significant.

3B.4) Results

Regression analysis of the growth curves clearly demonstrated differences in body weight gain for the four treatment groups (see Table 1). Dexamethasone significantly reduced final body weight and final body length; [Aib$^2$, Glu$^3$(NH-hexyl)]hGhrelin(1-28)-NH$_2$ (SEQ ID NO:2) increased linear growth in saline-treated rats and reversed growth inhibition in dexamethasone-treated rats (see Table 1). The inhibitory effects of dexamethasone on somatic growth was paralleled by decreased 24 hour food intake, diminished food efficiency (defined as a ratio between body weight gain and food intake measured over the same time interval) and lowered plasma IGF-1 levels when compared to vehicle-treated rats. [Aib$^2$, Glu$^3$(NH-hexyl)]hGhrelin(1-28)-NH$_2$ (SEQ ID NO:2) induced an increase in food intake and efficiency and plasma IGF-1 in saline-treated rats, and reversed the inhibitory effects of dexamethasone (see Table 2, FIG. 4). These results demonstrated that [Aib$^2$, Glu$^3$(NH-hexyl)]hGhrelin(1-28)-NH$_2$ (SEQ ID NO:2) is a therapeutic option to reverse the catabolic effects induced by glucocorticoids.

showed a linear increase of body weight vs time (P<0.05); actually, the slope of the growth curve that means the growth rate reported in Table 1, was significantly lower in dexamethasone-treated rats and greater in [Aib$^2$, Glu$^3$(NH-hexyl)] hGhrelin(1-28)-NH$_2$-treated (SEQ ID NO:2) rats as compared with saline-treated animals; the latter group grew at a rate indicative of normal growth. The growth rate of rats receiving both dexamethasone and [Aib$^2$, Glu$^3$(NH-hexyl)] hGhrelin(1-28)-NH$_2$ (SEQ ID NO:2) did not differ significantly from the value measured for the saline-treated group. Similar effects were observed when the experimental groups were analyzed for the final body weight and final nose-anal length. Any of the different pharmacological treatments did not alter significantly either the index of obesity (Lee index) or the weight of epididymal fat pads (Table 1).

Dexamethasone administration did not significantly affect cumulative 24-hour food intake up to 10 days from the beginning of the treatment (data not shown). After that time, a significant reduction in the amount of food consumed by dexamethasone-treated test subjects was observed compared to the amount consumed by the saline-treated animals; [Aib$^2$, Glu$^3$(NH-hexyl)]hGhrelin(1-28)-NH$_2$-treated (SEQ ID NO:2) subjects showed increased daily food intake when compared with saline-treated animals; food consumption for test subjects receiving both dexamethasone and [Aib$^2$, Glu$^3$ (NH-hexyl)]hGhrelin(1-28)-NH$_2$ (SEQ ID NO:2) did not differ significantly from saline only-treated animals with respect to feeding behavior (FIG. 4A). Food efficiency was calculated as the ratio between body weight gain (in grams) and food intake (in grams) measured over the same time interval. As shown in FIG. 4B, dexamethasone treatment significantly

TABLE 1

The effects of different pharmacological treatments on various growth parameters.

| Treatment | Final Body Weight (g) | Growth Rate (g/day) | Lee Obesity Index | Final Nose-Anal Length (cm) | Epididymal Fat Pads (g) |
| --- | --- | --- | --- | --- | --- |
| Saline | 211.1 ± 3.2 | 6.7 ± 0.3 | 322 ± 3.7 | 18.5 ± 0.2 | 1.23 ± 0.06 |
| A^ | 230.8 ± 4.8* | 7.6 ± 0.3** | 318 ± 1.4 | 19.3 ± 0.1** | 1.31 ± 0.07 |
| Dexamethasone | 185.2 ± 4.2** | 5.6 ± 0.2** | 321 ± 1.6 | 17.8 ± 0.2** | 1.14 ± 0.06 |
| Dexamethasone & A^ | 196.1 ± 4.7 | 6.2 ± 0.3 | 317 ± 2.9 | 18.3 ± 2.9 | 1.22 ± 0.1 |

All data are expressed as means ± SEM of eight animals for each experimental group.
*= P < 0.05;
**= P < 0.01 vs saline-treated rats (Dunnett's test).
A^ = [Aib$^2$, Glu$^3$(NH-hexyl)]hGhrelin(1-28)-NH$_2$(SEQ ID NO: 2).

TABLE 2

The effects of different pharmacological treatments on plasma hormones and glucose concentrations.

| Treatment | Corticosterone (ng/ml) | IGF-1 (ng/ml) | Insulin (μIU/ml) | Glucose (mg/dl) |
| --- | --- | --- | --- | --- |
| Saline | 125 ± 27 | 1464 ± 112 | 45.7 ± 4.1 | 120 ± 4 |
| A^ | 235 ± 23* | 1653 ± 87** | 40.4 ± 5.7 | 122 ± 3 |
| Dexamethasone | 19 ± 2*** | 1257 ± 112** | 50 ± 6 | 107 ± 6* |
| Dexamethasone & A^ | 22 ± 3*** | 1375 ± 89 | 63 ± 4.9* | 103 ± 5** |

All data are expressed as means ± SEM of eight animals for each experimental group.
*= P < 0.05;
**= P < 0.01;
***= P < 0.001 vs saline-treated rats (Dunnett's test).
A^ = [Aib$^2$, Glu$^3$(NH-hexyl)]hGhrelin(1-28)-NH$_2$(SEQ ID NO: 2).

Figure 3:
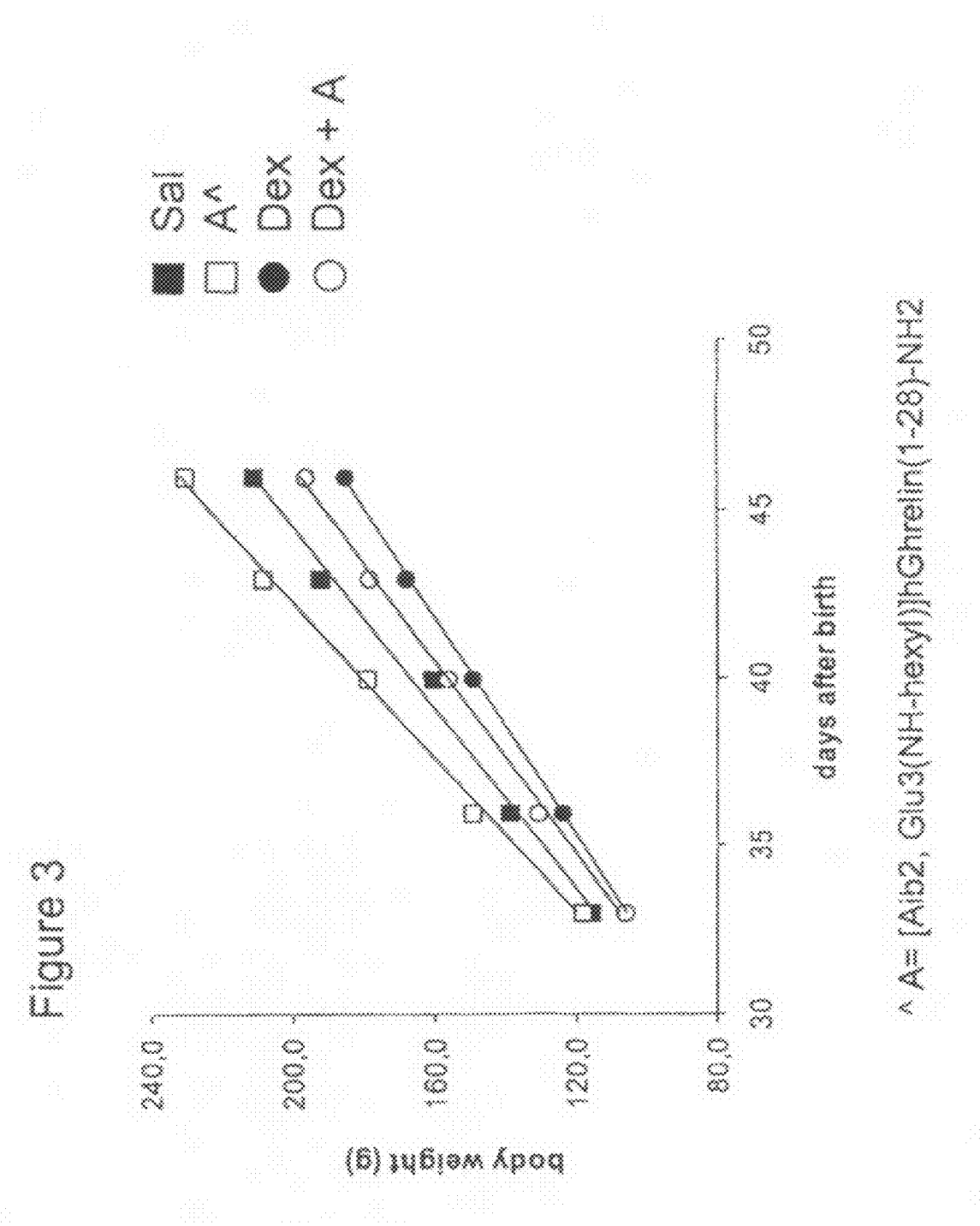
FIG. 3. The effect of the different pharmacological treatment on somatic growth in young male rats, dexamethasone (also referred to herein as "DEX") treatment significantly decreased (P<0.01) somatic growth whereas [Aib$^2$, Glu$^3$(NH-hexyl)]hGhrelin(1-28)-NH$_2$ (SEQ ID NO:2) (indicated as "A") administration significantly increased (P<0.05) somatic growth as compared to SAL-treated rats. The growth suppression induced by DEX was reversed by concomitant [Aib$^2$, Glu$^3$(NH-hexyl)]hGhrelin(1-28)-NH$_2$ (SEQ ID NO:2) treatment (Dunnett's t test for multiple comparisons). Data represent the mean of eight animals; Straight lines represent the linear regression analysis (R=0.9, P<0.05 for all the experimental groups).

The effects of chronic glucocorticoid treatment on somatic growth are illustrated in FIG. 3 and described in Table 1. Regression analysis of the data obtained during the complete treatment period demonstrated that all experimental groups reduced food efficiency whereas [Aib$^2$, Glu$^3$(NH-hexyl)] hGhrelin(1-28)-NH$_2$ (SEQ ID NO:2) treatment increased food efficiency as compared with saline treatment in two out of three determinations; it was observed that [Aib$^2$, Glu$^3$(NH-hexyl)]hGhrelin(1-28)-NH$_2$ (SEQ ID NO:2) administration was able to reverse the decrease of food efficiency induced by dexamethasone. It was found that food efficiency decreased with age in all the experimental groups (P<0.05); on the third determination, all values tended to a minimum without significant differences between the experimental groups.

The effects of the different pharmacological treatments on plasma hormones and glucose levels measured at the moment of sacrificing the test subjects are described in Table 2. As expected, chronic dexamethasone administration suppressed almost completely corticosterone secretion and significantly reduced plasma IGF-1 concentration as compared with saline. The preferred ghrelin analog, [Aib$^2$, Glu$^3$(NH-hexyl)]hGhrelin(1-28)-NH$_2$ (SEQ ID NO:2), induced a clear-cut increase of plasma corticosterone in saline-treated animals as compared with those treated only with the vehicle, but was not able to overcome the suppression of the HPA axis due to negative feedback in dexamethasone-treated animals. [Aib$^2$, Glu$^3$(NH-hexyl)]hGhrelin(1-28)-NH$_2$-treated (SEQ ID NO:2) subjects showed higher IGF-1 levels compared to saline-treated animals; [Aib$^2$, Glu$^3$(NH-hexyl)]hGhrelin(1-28)-NH$_2$ (SEQ ID NO:2) partially reversed IGF-1 suppression in dexamethasone-treated subjects. Dexamethasone treatment tended to increase plasma insulin concentration, but the effect did not reach statistical significance. [Aib$^2$, Glu$^3$(NH-hexyl)]hGhrelin(1-28)-NH$_2$ (SEQ ID NO:2) administration kept plasma insulin levels unchanged in the saline-treated animals as compared with vehicle; the simultaneous administration of dexamethasone and [Aib$^2$, Glu$^3$(NH-hexyl)]hGhrelin(1-28)-NH$_2$ (SEQ ID NO:2) significantly induced insulin secretion and the increase of plasma insulin was paralleled by a decrease of plasma glucose levels.

The day before the end of the experiment, glucose levels were measured in blood samples collected from the tail vein at three times during the light phase of the daily cycle (10:00 am, 3:00 pm and 6:00 pm). All of the subjects of the experimental groups were euglycemic with minor changes with respect to the mean values of plasma glucose recorded at the moment of the decapitation (see Table 2).

Figure 5:
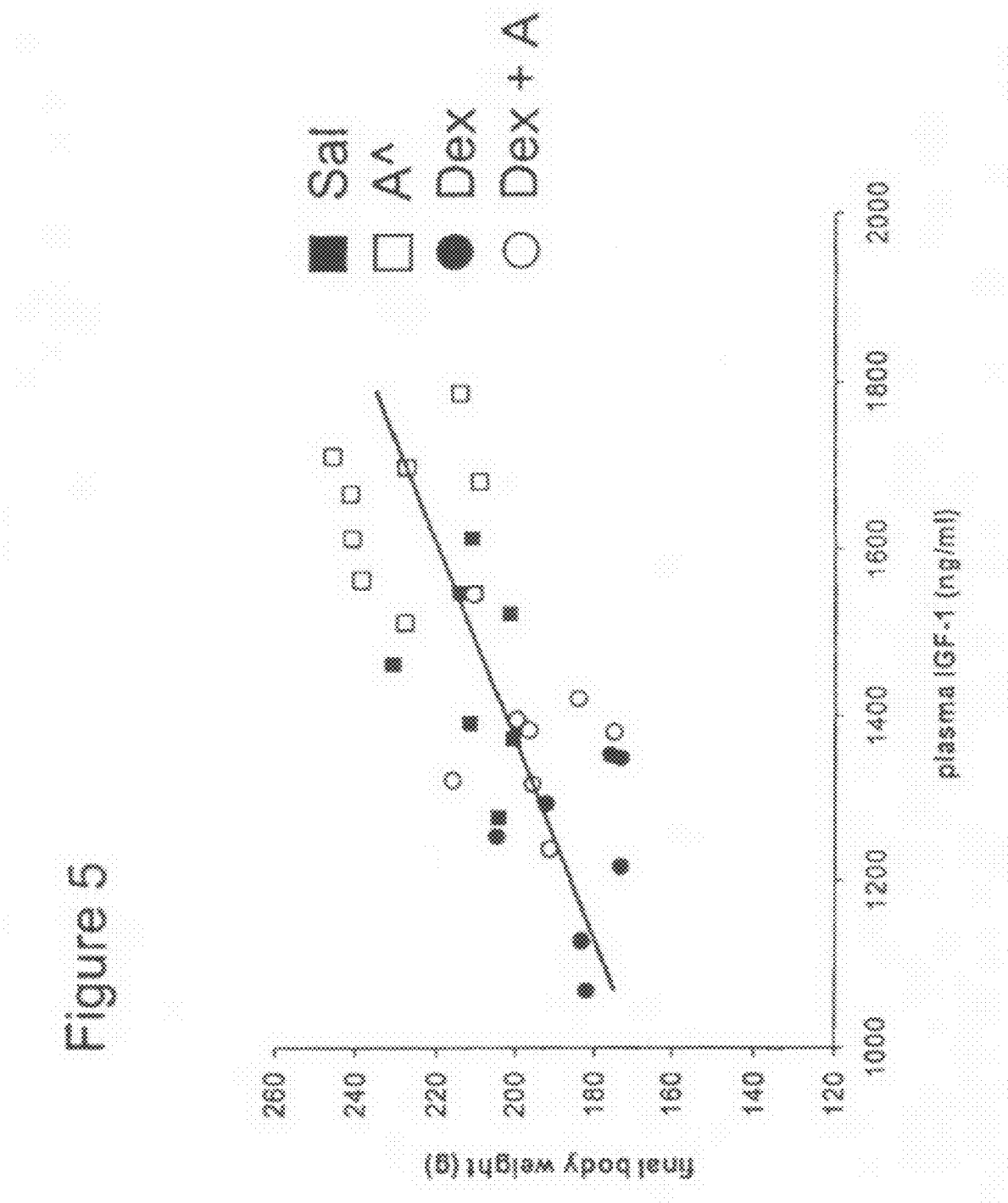
FIG. 5. Study of the relationship between the final body weight and plasma IGF-1 concentration at the moment of the killing of the rats: a positive linear correlation was observed (N=32, two tailed Pearson R=0.7125, P<0.001); dotted square, SAL; open square, [Aib$^2$, Glu$^3$(NH-hexyl)]hGhrelin(1-28)-NH (SEQ ID NO:2); dotted circle, DEX; open circle, DEX+[Aib$^2$, Glu$^3$(NH-hexyl)]hGhrelin(1-28)-NH$_2$ (SEQ ID NO:2).

A positive correlation between plasma IGF-1 concentration and final body weight, plotting the values of all the animals without taking into account the different pharmacological treatment (N=32, two tailed Pearson R=0.7125, P<0.001; FIG. 5) was observed. A positive linear correlation between plasma insulin levels and final body weight, limiting the analysis to test subjects treated simultaneously with dexamethasone and [Aib$^2$, Glu$^3$(NH-hexyl)]hGhrelin(1-28)-NH$_2$ (SEQ ID NO:2) or its vehicle (N=16, two tailed Pearson R=0.5848, P<0.05), is illustrated in FIG. 6. No relationship was observed between plasma insulin and final body weight, limiting the analysis to saline-treated animals. (FIG. 4).

The main implications of the results shown in this preclinical study is that stabilized ghrelin analogs may have clinical application to counteract the catabolic state induced by long-term glucocorticoid therapy. The reversal of glucocorticoid inhibition of growth in young rats, following the ghrelin analog administration, was mediated by enhanced food efficiency and increased circulating IGF-1 levels, an index of somatotropic axis activity; the positive correlation observed between plasma insulin concentration and final body weight suggest that insulin as well might have had a key role in mediating the anabolic effects of ghrelin in dexamethasone-treated rats. Noteworthy, it has been proved that ghrelin in vitro potentates the cellular response to insulin.

The main drawback to the use of ghrelin in dexamethasone-treated patients might be the increase of visceral adiposity due to ghrelin's adipogenic effect and the reduction of glucose tolerance through the sustained stimulation of GH release. The results reported herein argue against this hypothesis since the plasma glucose levels during the light phase and the weight of the epididymal fat pads, an index of abdominal fat depots, did not differ significantly between the experimental groups after three weeks of treatment. It is important to note that the present experiment differs from prior studies dealing with the metabolic and adipogenic effects of ghrelin in a rat model since the ghrelin analogue was administered to pre-pubertal test subjects. It is well-known that rodents, at this age, grow rapidly with linear somatic growth; thus suggesting that the selected subjects may be less prone to accumulate fat mass compare to more mature test subjects having reduced growth rates.

Administration

Ghrelin analogs, in particular [Aib$^2$, Glu$^3$(NH-hexyl)]hGhrelin(1-28)-NH$_2$ (SEQ ID NO:2), can be formulated and administered to a subject using the guidance provided herein along with techniques well known in the art. The preferred route of administration ensures that an effective amount of compound reaches the target. Guidelines for pharmaceutical administration in general are provided in, for example, Remington's Pharmaceutical Sciences 18$^{th}$ Edition, Ed. Gennaro, Mack Publishing, 1990, and Modem Pharmaceutics 2$^{nd}$ Edition, Eds. Banker and Rhodes, Marcel Dekker, Inc., 1990, both of which are hereby incorporated by reference herein.

Ghrelin analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Ghrelin analogs can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

Ghrelin analogs may also be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Ghrelin analogs can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The invention claimed is:

1. A method to ameliorate the catabolic effects of excess glucocorticoids in a child in need of such treatment comprising administering to said child a therapeutically effective amount of a ghrelin agonist, wherein said excess glucocorticoids are the result of the long term administration of dexamethasone.

2. A method according to claim 1, wherein said amelioration alleviates a reduction in growth in said child.

3. A method according to claim 1, wherein said amelioration alleviates a reduction in growth rate in said child.

4. A method according to claim 1, wherein said amelioration alleviates a reduction in body weight in said child.

5. A method according to claim 1, wherein said amelioration alleviates a reduction in body weight due in part to a loss in lean body mass in said child.

6. A method according to claim 1, wherein said amelioration alleviates a reduction in IGF-1 levels in said child.

7. A method according to claim 1, wherein said amelioration alleviates a reduction in bone mass in said child.

8. A method according to claim 1 wherein said ghrelin agonist is [Aib$^2$, Glu$^3$(NH-hexyl)]hGhrelin(1-28)-NH$_2$ (SEQ ID NO:2).

9. A method according to claim 1 wherein said ghrelin agonist is selecting from the group consisting of:

(Dap$^3$(octanesulfonyl))hGhrelin(1-28)-NH$_2$ (SEQ ID NO: 3)

(Aib$^2$, A6c$^5$)hGhrelin(1-28)-NH$_2$ (SEQ ID NO: 4)

(Aib$^{2,6}$)hGhrelin(1-28)-NH$_2$ (SEQ ID NO: 5)

(Aib$^2$, 3-Pal$^9$)hGhrelin(1-28)-NH$_2$ (SEQ ID NO: 6)

(A5c$^2$)hGhrelin(1-28)-NH$_2$ (SEQ ID NO: 7)

(Act$^2$)hGhrelin(1-28)-NH$_2$ (SEQ ID NO: 8)

(Aib$^2$, Act$^6$)hGhrelin(1-28)-NH$_2$ (SEQ ID NO: 9)

(Aib$^2$, Abu$^6$)hGhrelin(1-28)-NH$_2$ (SEQ ID NO: 10)

(Aib$^2$, 4-Hyp$^7$)hGhrelin(1-28)-NH$_2$ (SEQ ID NO: 11)

(Aib$^2$, Thz$^7$)hGhrelin(1-28)-NH$_2$ (SEQ ID NO: 12)

(Aib$^2$, Pip$^7$)hGhrelin(1-28)-NH$_2$ (SEQ ID NO: 13)

(Aib$^2$, Dhp$^7$)hGhrelin(1-28)-NH$_2$ (SEQ ID NO: 14)

(Aib$^{2,8}$)hGhrelin(1-28)-NH$_2$ (SEQ ID NO: 15)

(Aib$^2$, 4-Pal$^9$)hGhrelin(1-28)-NH$_2$ (SEQ ID NO: 16)

(Aib$^2$, Taz$^9$)hGhrelin(1-28)-NH$_2$ (SEQ ID NO: 17)

(Aib$^{2,10}$)hGhrelin(1-28)-NH$_2$ (SEQ ID NO: 18)

-continued (Aib$^2$, Tic$^7$)hGhrelin(1-28)-NH$_2$ (SEQ ID NO: 19)

(A6c$^5$)hGhrelin(1-28)-NH$_2$ (SEQ ID NO: 20)

(3-Pal$^9$)hGhrelin(1-28)-NH$_2$ (SEQ ID NO: 21)

(Aib$^8$)hGhrelin(1-28)-NH$_2$ (SEQ ID NO: 22)

(2-Thi$^9$)hGhrelin(1-28)-NH$_2$ (SEQ ID NO: 23)

(Aib$^2$, Cha$^5$)hGhrelin(1-28)-NH$_2$ (SEQ ID NO: 24)

(Aib$^2$, Glu$^3$(NH-hexyl), 4-Hyp$^7$)hGhrelin(1-28)-NH$_2$ (SEQ ID NO: 25)

((Aib$^{2,8}$, Glu$^3$(NH-hexyl))hGhrelin(1-28)-NH$_2$ (SEQ ID NO: 26)

(Aib$^2$, Glu$^3$(NH-hexyl), 3-Pal9)hGhrelin(1-28)-NH$_2$ (SEQ ID NO: 27)

(Aib$^2$, Glu$^3$(NH-hexyl), 4-Pal9)hGhrelin(1-28)-NH$_2$ (SEQ ID NO: 28)

(Aib$^2$, Glu$^3$(NH-hexyl), Taz$^9$)hGhrelin(1-28)-NH$_2$ (SEQ ID NO: 29)

(Aib$^2$, Glu$^3$(NH-hexyl), 2-Thi$^9$)hGhrelin(1-28)-NH$_2$ (SEQ ID NO: 30)

(Aib$^{2,10}$, Glu$^3$(NH-hexyl))hGhrelin(1-28)-NH$_2$ (SEQ ID NO: 31)

(Glu$^3$(NH-hexyl), 4-Hyp$^7$)hGhrelin(1-28)-NH$_2$ (SEQ ID NO: 32)

(Glu$^3$(NH-hexyl), Aib$^8$)hGhrelin(1-28)-NH$_2$ (SEQ ID NO: 33)

(Aib$^{2,12}$, Glu$^3$(NH-hexyl), 4-Pal$^9$, Orn$^{15}$)hGhrelin(1-28)-NH$_2$ (SEQ ID NO: 34)

(Glu$^3$(O-hexyl))hGhrelin(1-28)-NH$_2$ (SEQ ID NO: 35)

(Aib$^2$)hGhrelin(1-28)-NH$_2$ (SEQ ID NO: 36)

(Glu$^3$(NH-hexyl))hGhrelin(1-28)-NH$_2$ (SEQ ID NO: 37)

(Ac-Gly$^1$, Aib$^2$)hGhrelin(1-28)-NH$_2$ (SEQ ID NO: 38)

and (n-octanoyl-Gly$^1$)hGhrelin(1-28)-NH$_2$. (SEQ ID NO: 41)

10. A method according to claim 1, wherein the administration of said ghrelin agonist is selected from the group consisting of subcutaneous, intramuscular, intranasal, intraperitoneal, and intravenous administration.

11. A method for allowing the long term administration of therapeutic doses of dexamethasone to a child to treat a disease or condition, comprising alleviating the catabolic effects of the administration of said long term therapeutic doses of dexamethasone by the administration of a ghrelin agonist.

12. A method according to claim 11, in which said ghrelin agonist is [Aib$^2$, Glu$^3$(NH-hexyl)]hGhrelin(1-28)-NH$_2$ (SEQ ID NO:2).

13. A method according to claim 11, wherein said ghrelin agonist is selecting from the group consisting of:

(Dap³(octanesulfonyl))hGhrelin(1-28)-NH₂ (SEQ ID NO: 3)

(Aib², A6c⁵)hGhrelin(1-28)-NH₂ (SEQ ID NO: 4)

(Aib²,⁶)hGhrelin(1-28)-NH₂ (SEQ ID NO: 5)

(Aib², 3-Pal⁹)hGhrelin(1-28)-NH₂ (SEQ ID NO: 6)

(A5c²)hGhrelin(1-28)-NH₂ (SEQ ID NO: 7)

(Act²)hGhrelin(1-28)-NH₂ (SEQ ID NO: 8)

(Aib², Act⁶)hGhrelin(1-28)-NH₂ (SEQ ID NO: 9)

(Aib², Abu⁶)hGhrelin(1-28)-NH₂ (SEQ ID NO: 10)

(Aib², 4-Hyp⁷)hGhrelin(1-28)-NH₂ (SEQ ID NO: 11)

(Aib², Thz⁷)hGhrelin(1-28)-NH₂ (SEQ ID NO: 12)

(Aib², Pip⁷)hGhrelin(1-28)-NH₂ (SEQ ID NO: 13)

(Aib², Dhp⁷)hGhrelin(1-28)-NH₂ (SEQ ID NO: 14)

(Aib²,⁸)hGhrelin(1-28)-NH₂ (SEQ ID NO: 15)

(Aib², 4-Pal⁹)hGhrelin(1-28)-NH₂ (SEQ ID NO: 16)

(Aib², Taz⁹)hGhrelin(1-28)-NH₂ (SEQ ID NO: 17)

(Aib²,¹⁰)hGhrelin(1-28)-NH₂ (SEQ ID NO: 18)

(Aib², Tic⁷)hGhrelin(1-28)-NH₂ (SEQ ID NO: 19)

(A6c⁵)hGhrelin(1-28)-NH₂ (SEQ ID NO: 20)

(3-Pal⁹)hGhrelin(1-28)-NH₂ (SEQ ID NO: 21)

(Aib⁸)hGhrelin(1-28)-NH₂ (SEQ ID NO: 22)

(2-Thi⁹)hGhrelin(1-28)-NH₂ (SEQ ID NO: 23)

(Aib², Cha⁵)hGhrelin(1-28)-NH₂ (SEQ ID NO: 24)

(Aib², Glu³(NH-hexyl), 4-Hyp⁷)hGhrelin(1-28)-NH₂ (SEQ ID NO: 25)

((Aib²,⁸, Glu³(NH-hexyl))hGhrelin(1-28)-NH₂ (SEQ ID NO: 26)

(Aib², Glu³(NH-hexyl), 3-Pal9)hGhrelin(1-28)-NH₂ (SEQ ID NO: 27)

(Aib², Glu³(NH-hexyl), 4-Pal9)hGhrelin(1-28)-NH₂ (SEQ ID NO: 28)

(Aib², Glu³(NH-hexyl), Taz⁹)hGhrelin(1-28)-NH₂ (SEQ ID NO: 29)

(Aib², Glu³(NH-hexyl), 2-Thi⁹)hGhrelin(1-28)-NH₂ (SEQ ID NO: 30)

(Aib²,¹⁰, Glu³(NH-hexyl))hGhrelin(1-28)-NH₂ (SEQ ID NO: 31)

(Glu³(NH-hexyl), 4-Hyp⁷)hGhrelin(1-28)-NH₂ (SEQ ID NO: 32)

(Glu³(NH-hexyl), Aib⁸)hGhrelin(1-28)-NH₂ (SEQ ID NO: 33)

(Aib²,¹², Glu³(NH-hexyl), 4-Pal⁹, Orn¹⁵)hGhrelin(1-28)-NH₂ (SEQ ID NO: 34)

(Glu³(O-hexyl))hGhrelin(1-28)-NH₂ (SEQ ID NO: 35)

(Aib²)hGhrelin(1-28)-NH₂ (SEQ ID NO: 36)

(Glu³(NH-hexyl))hGhrelin(1-28)-NH₂ (SEQ ID NO: 37)

(Ac-Gly¹, Aib²)hGhrelin(1-28)-NH₂ (SEQ ID NO: 38)

and (n-octanoyl-Gly¹)hGhrelin(1-28)-NH₂ (SEQ ID NO: 41).

14. A method according to claim 11, wherein said therapeutic doses of dexamethasone are administered to a child to treat respiratory distress of prematurity and said catabolic effects of said long term administration of therapeutic doses of dexamethasone are alleviated by the administration of a ghrelin agonist.

15. A method according to claim 14, in which said ghrelin agonist is [Aib², Glu³(NH-hexyl)]hGhrelin(1-28)-NH₂ (SEQ ID NO:2).

16. A method according to claim 14, wherein said ghrelin agonist is selecting from the group consisting of:

(Dap³(octanesulfonyl))hGhrelin(1-28)-NH₂ (SEQ ID NO: 3)

(Aib², A6c⁵)hGhrelin(1-28)-NH₂ (SEQ ID NO: 4)

(Aib²,⁶)hGhrelin(1-28)-NH₂ (SEQ ID NO: 5)

(Aib², 3-Pal⁹)hGhrelin(1-28)-NH₂ (SEQ ID NO: 6)

(A5c²)hGhrelin(1-28)-NH₂ (SEQ ID NO: 7)

(Act²)hGhrelin(1-28)-NH₂ (SEQ ID NO: 8)

(Aib², Act⁶)hGhrelin(1-28)-NH₂ (SEQ ID NO: 9)

(Aib², Abu⁶)hGhrelin(1-28)-NH₂ (SEQ ID NO: 10)

(Aib², 4-Hyp⁷)hGhrelin(1-28)-NH₂ (SEQ ID NO: 11)

(Aib², Thz⁷)hGhrelin(1-28)-NH₂ (SEQ ID NO: 12)

(Aib², Pip⁷)hGhrelin(1-28)-NH₂ (SEQ ID NO: 13)

(Aib², Dhp⁷)hGhrelin(1-28)-NH₂ (SEQ ID NO: 14)

(Aib²,⁸)hGhrelin(1-28)-NH₂ (SEQ ID NO: 15)

(Aib², 4-Pal⁹)hGhrelin(1-28)-NH (SEQ ID NO: 16)

(Aib², Taz⁹)hGhrelin(1-28)-NH (SEQ ID NO: 17)

(Aib²,¹⁰)hGhrelin(1-28)-NH₂ (SEQ ID NO: 18)

(Aib², Tic⁷)hGhrelin(1-28)-NH₂ (SEQ ID NO: 19)

(A6c⁵)hGhrelin(1-28)-NH₂ (SEQ ID NO: 20)

(3-Pal⁹)hGhrelin(1-28)-NH₂ (SEQ ID NO: 21)

(Aib⁸)hGhrelin(1-28)-NH₂ (SEQ ID NO: 22)

(2-Thi⁹)hGhrelin(1-28)-NH₂ (SEQ ID NO: 23)

(Aib², Cha⁵)hGhrelin(1-28)-NH₂ (SEQ ID NO: 24)

(Aib², Glu³(NH-hexyl), 4-Hyp⁷)hGhrelin(1-28)-NH₂ (SEQ ID NO: 25)

((Aib²,⁸, Glu³(NH-hexyl))hGhrelin(1-28)-NH₂ (SEQ ID NO: 26)

(Aib², Glu³(NH-hexyl), 3-Pal9)hGhrelin(1-28)-NH₂ (SEQ ID NO: 27)

(Aib², Glu³(NH-hexyl), 4-Pal9)hGhrelin(1-28)-NH₂ (SEQ ID NO: 28)

(Aib², Glu³(NH-hexyl), Taz⁹)hGhrelin(1-28)-NH₂ (SEQ ID NO: 29)

(Aib², Glu³(NH-hexyl), 2-Thi⁹)hGhrelin(1-28)-NH₂ (SEQ ID NO: 30)

(Aib²,¹⁰, Glu³(NH-hexyl))hGhrelin(1-28)-NH₂ (SEQ ID NO: 31)

(Glu³(NH-hexyl), 4-Hyp⁷)hGhrelin(1-28)-NH₂ (SEQ ID NO: 32)

(Glu³(NH-hexyl), Aib⁸)hGhrelin(1-28)-NH₂ (SEQ ID NO: 33)

(Aib²,¹², Glu³(NH-hexyl), 4-Pal⁹, Orn¹⁵)hGhrelin(1-28)-NH₂ (SEQ ID NO: 34)

(Glu³(O-hexyl))hGhrelin(1-28)-NH₂ (SEQ ID NO: 35)

(Aib²)hGhrelin(1-28)-NH₂ (SEQ ID NO: 36)

(Glu³(NH-hexyl))hGhrelin(1-28)-NH₂ (SEQ ID NO: 37)

(Ac-Gly¹, Aib²)hGhrelin(1-28)-NH₂ (SEQ ID NO: 38)

and (n-octanoyl-Gly¹)hGhrelin(1-28)-NH₂. (SEQ ID NO: 41)

17. A method according to claim 11, wherein said therapeutic doses of dexamethasone are administered to a child to treat asthma and said catabolic effects of said long term administration of therapeutic doses of dexamethasone are alleviated by the administration of a ghrelin agonist.

18. A method according to claim 17, in which said ghrelin agonist is [Aib², Glu³(NH-hexyl)]hGhrelin(1-28)-NH₂ (SEQ ID NO:2).

19. A method according to claim 17, wherein said ghrelin agonist is selecting from the group consisting of:

(Dap³(octanesulfonyl))hGhrelin(1-28)-NH₂ (SEQ ID NO: 3)

(Aib², A6c⁵)hGhrelin(1-28)-NH₂ (SEQ ID NO: 4)

(Aib²,⁶)hGhrelin(1-28)-NH₂ (SEQ ID NO: 5)

(Aib², 3-Pal⁹)hGhrelin(1-28)-NH₂ (SEQ ID NO: 6)

(A5c²)hGhrelin(1-28)-NH₂ (SEQ ID NO: 7)

(Act²)hGhrelin(1-28)-NH₂ (SEQ ID NO: 8)

(Aib², Act⁶)hGhrelin(1-28)-NH₂ (SEQ ID NO: 9)

(Aib², Abu⁶)hGhrelin(1-28)-NH₂ (SEQ ID NO: 10)

(Aib², 4-Hyp⁷)hGhrelin(1-28)-NH₂ (SEQ ID NO: 11)

(Aib², Thz⁷)hGhrelin(1-28)-NH₂ (SEQ ID NO: 12)

(Aib², Pip⁷)hGhrelin(1-28)-NH₂ (SEQ ID NO: 13)

(Aib², Dhp⁷)hGhrelin(1-28)-NH₂ (SEQ ID NO: 14)

(Aib²,⁸)hGhrelin(1-28)-NH₂ (SEQ ID NO: 15)

(Aib², 4-Pal⁹)hGhrelin(1-28)-NH₂ (SEQ ID NO: 16)

(Aib², Taz⁹)hGhrelin(1-28)-NH₂ (SEQ ID NO: 17)

(Aib²,¹⁰)hGhrelin(1-28)-NH₂ (SEQ ID NO: 18)

(Aib², Tic⁷)hGhrelin(1-28)-NH₂ (SEQ ID NO: 19)

(A6c⁵)hGhrelin(1-28)-NH₂ (SEQ ID NO: 20)

(3-Pal⁹)hGhrelin(1-28)-NH₂ (SEQ ID NO: 21)

(Aib⁸)hGhrelin(1-28)-NH₂ (SEQ ID NO: 22)

(2-Thi⁹)hGhrelin(1-28)-NH₂ (SEQ ID NO: 23)

(Aib², Cha⁵)hGhrelin(1-28)-NH₂ (SEQ ID NO: 24)

(Aib², Glu³(NH-hexyl), 4-Hyp⁷)hGhrelin(1-28)-NH₂ (SEQ ID NO: 25)

((Aib²,⁸, Glu³(NH-hexyl))hGhrelin(1-28)-NH₂ (SEQ ID NO: 26)

(Aib², Glu³(NH-hexyl), 3-Pal9)hGhrelin(1-28)-NH₂ (SEQ ID NO: 27)

(Aib², Glu³(NH-hexyl), 4-Pal9)hGhrelin(1-28)-NH₂ (SEQ ID NO: 28)

(Aib², Glu³(NH-hexyl), Taz⁹)hGhrelin(1-28)-NH₂ (SEQ ID NO: 29)

(Aib², Glu³(NH-hexyl), 2-Thi⁹)hGhrelin(1-28)-NH₂ (SEQ ID NO: 30)

(Aib²,¹⁰, Glu³(NH-hexyl))hGhrelin(1-28)-NH₂ (SEQ ID NO: 31)

(Glu³(NH-hexyl), 4-Hyp⁷)hGhrelin(1-28)-NH₂ (SEQ ID NO: 32)

(Glu³(NH-hexyl), Aib⁸)hGhrelin(1-28)-NH₂ (SEQ ID NO: 33)

(Aib²,¹², Glu³(NH-hexyl), 4-Pal⁹, Orn¹⁵)hGhrelin(1-28)-NH₂ (SEQ ID NO: 34)

(Glu³(O-hexyl))hGhrelin(1-28)-NH₂ (SEQ ID NO: 35)

(Aib²)hGhrelin(1-28)-NH₂ (SEQ ID NO: 36)

(Glu³(NH-hexyl))hGhrelin(1-28)-NH₂ (SEQ ID NO: 37)

(Ac-Gly¹, Aib²)hGhrelin(1-28)-NH₂ (SEQ ID NO: 38)

and (n-octanoyl-Gly¹)hGhrelin(1-28)-NH₂ (SEQ ID NO: 41).

20. A method according to claim 11, wherein said administration of said ghrelin agonist is selected from the group consisting of subcutaneous, intramuscular, intranasal, intraperitoneal, and intravenous administration.

* * * * *

SEQUENCE LISTING

```
<160> NUMBER OF SEQ ID NOS: 129

<210> SEQ ID NO 1
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: AMIDATION

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 2

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 28
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MISC_FEATURE
<222> LOCATION: (3)..(3)
<223> OTHER INFORMATION: Xaa = 2,3-diaminopropionic acid (Dap) modified
      with octanesulfonyl
<220> FEATURE:
<221> NAME/KEY: MOD_RES
<222> LOCATION: (28)..(28)
<223> OTHER INFORMATION: AMIDATION

<400> SEQUENCE: 3

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MOD_RES
<222> LOCATION: (28)..(28)
<223> OTHER INFORMATION: AMIDATION

<400> SEQUENCE: 4

Gly Xaa Ser Phe Xaa Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 5
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 5

Gly Xaa Ser Phe Leu Xaa Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Artificial Sequence
<220> FEATURE:
```

-continued

<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(3-pyridinyl)Ala (3Pal)
<220> FEATURE:
<221> NAME/KEY: MOD_RES
<222> LOCATION: (28)..(28)
<223> OTHER INFORMATION: AMIDATION

<400> SEQUENCE: 6

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 7
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
      (A5c)
<220> FEATURE:
<221> NAME/KEY: MOD_RES
<222> LOCATION: (28)..(28)
<223> OTHER INFORMATION: AMIDATION

<400> SEQUENCE: 7

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 8
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = 4-amino-4-carboxytetrahydropyran (Act)
<220> FEATURE:
<221> NAME/KEY: MOD_RES
<222> LOCATION: (28)..(28)
<223> OTHER INFORMATION: AMIDATION

<400> SEQUENCE: 8

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 9
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE

```
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = 4-amino-4-carboxytetrahydropyran (Act)
<220> FEATURE:
<221> NAME/KEY: MOD_RES
<222> LOCATION: (28)..(28)
<223> OTHER INFORMATION: AMIDATION

<400> SEQUENCE: 9

Gly Xaa Ser Phe Leu Xaa Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (6)..(6)
<223> OTHER INFORMATION: Xaa = alpha-aminobutyric acid (Abu)
<220> FEATURE:
<221> NAME/KEY: MOD_RES
<222> LOCATION: (28)..(28)
<223> OTHER INFORMATION: AMIDATION

<400> SEQUENCE: 10

Gly Xaa Ser Phe Leu Xaa Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 11
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 4-hydroxyPro (4Hyp)
<220> FEATURE:
<221> NAME/KEY: MOD_RES
<222> LOCATION: (28)..(28)
<223> OTHER INFORMATION: AMIDATION

<400> SEQUENCE: 11

Gly Xaa Ser Phe Leu Ser Xaa Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 12
<211> LENGTH: 28
<212> TYPE: PRT
<213> ORGANISM: Artificial sequence
```

```
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = thiazolidine-4-carboxylic acid (Thz)
<220> FEATURE:
<221> NAME/KEY: MOD_RES
<222> LOCATION: (28)..(28)
<223> OTHER INFORMATION: AMIDATION

<400> SEQUENCE: 12

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 13
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = pipecolic acid (Pip)
<220> FEATURE:
<221> NAME/KEY: MOD_RES
<222> LOCATION: (28)..(28)
<223> OTHER INFORMATION: AMIDATION

<400> SEQUENCE: 13

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 14
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 3,4-dehydroPro (Dhp)
<220> FEATURE:
<221> NAME/KEY: MOD_RES
<222> LOCATION: (28)..(28)
<223> OTHER INFORMATION: AMIDATION

<400> SEQUENCE: 14

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 15
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 15

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 16
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(4-pyridinyl)Ala (4Pal)
<220> FEATURE:
<221> NAME/KEY: MOD_RES
<222> LOCATION: (28)..(28)
<223> OTHER INFORMATION: AMIDATION

<400> SEQUENCE: 16

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 17
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (9)..(9)
<223> OTHER INFORMATION: Xaa = beta-(4-thiazolyl)Ala (Taz)
<220> FEATURE:
<221> NAME/KEY: MOD_RES
<222> LOCATION: (28)..(28)
<223> OTHER INFORMATION: AMIDATION

<400> SEQUENCE: 17

Gly Xaa Ser Phe Leu Ser Pro Glu Xaa Gln Arg Val Gln Gln Arg Lys
1               5                   10                  15
```

```
Glu Ser Lys Lys Pro Pro Ala Lys Leu Gln Pro Arg
            20                  25

<210> SEQ ID NO 18
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 18

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 19
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (7)..(7)
<223> OTHER INFORMATION: Xaa = 1,2,3,4-tetrahydroisoquinoline-3-
      carboxylic acid (Tic)
<220> FEATURE:
<221> NAME/KEY: MOD_RES
<222> LOCATION: (28)..(28)
<223> OTHER INFORMATION: AMIDATION

<400> SEQUENCE: 19

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 20
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (5)..(5)
<223> OTHER INFORMATION: Xaa = 1-amino-1-cyclohexanecarboxylic acid
      (A6c)
<220> FEATURE:
<221> NAME/KEY: MOD_RES
<222> LOCATION: (28)..(28)
<223> OTHER INFORMATION: AMIDATION

<400> SEQUENCE: 20

Gly Ser Ser Phe Xaa Ser Pro Glu His Gln Arg Val Gln Gln Arg Lys
```

Glu Ser Lys Lys Pro Pro Ala Lys Leu Gln Pro Arg
            20                  25

<210> SEQ ID NO 21
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (9)..(9)
<223> OTHER INFORMATION: Xaa = beta-(3-pyridinyl)Ala (3Pal)
<220> FEATURE:
<221> NAME/KEY: MOD_RES
<222> LOCATION: (28)..(28)
<223> OTHER INFORMATION: AMIDATION

<400> SEQUENCE: 21

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 22
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 22

Gly Ser Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 23
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (9)..(9)
<223> OTHER INFORMATION: Xaa = beta-(2-thienyl) Ala (2-Thi)
<220> FEATURE:
<221> NAME/KEY: MOD_RES
<222> LOCATION: (28)..(28)
<223> OTHER INFORMATION: AMIDATION

<400> SEQUENCE: 23

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 24
<211> LENGTH: 28

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (5)..(5)
<223> OTHER INFORMATION: Xaa = beta-cyclohexylAla (Cha)
<220> FEATURE:
<221> NAME/KEY: MOD_RES
<222> LOCATION: (28)..(28)
<223> OTHER INFORMATION: AMIDATION

<400> SEQUENCE: 24

Gly Xaa Ser Phe Xaa Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 25
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 4-hydroxyPro (4Hyp)
<220> FEATURE:
<221> NAME/KEY: MOD_RES
<222> LOCATION: (28)..(28)
<223> OTHER INFORMATION: AMIDATION

<400> SEQUENCE: 25

Gly Xaa Glu Phe Leu Ser Xaa Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 26
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION
```

-continued

<400> SEQUENCE: 26

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 27
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridiyl)Ala (3Pal)
<220> FEATURE:
<221> NAME/KEY: MOD_RES
<222> LOCATION: (28)..(28)
<223> OTHER INFORMATION: AMIDATION

<400> SEQUENCE: 27

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 28
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-pyridiyl)Ala (4Pal)
<220> FEATURE:
<221> NAME/KEY: MOD_RES
<222> LOCATION: (28)..(28)
<223> OTHER INFORMATION: AMIDATION

<400> SEQUENCE: 28

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Artificial sequence
<220> FEATURE:
<223> OTHER INFORMATION: Ghrelin analog

```
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)Ala (Taz)
<220> FEATURE:
<221> NAME/KEY: MOD_RES
<222> LOCATION: (28)..(28)
<223> OTHER INFORMATION: AMIDATION

<400> SEQUENCE: 29

Gly Xaa Glu Phe Leu Ser Pro Glu Xaa Gln Arg Val Gln Gln Arg Lys
 1               5                  10                  15

Glu Ser Lys Lys Pro Pro Ala Lys Leu Gln Pro Arg
            20                  25

<210> SEQ ID NO 30
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(2-thienyl)Ala (2-Thi)
<220> FEATURE:
<221> NAME/KEY: MOD_RES
<222> LOCATION: (28)..(28)
<223> OTHER INFORMATION: AMIDATION

<400> SEQUENCE: 30

Gly Xaa Glu Phe Leu Ser Pro Glu Xaa Gln Arg Val Gln Gln Arg Lys
 1               5                  10                  15

Glu Ser Lys Lys Pro Pro Ala Lys Leu Gln Pro Arg
            20                  25

<210> SEQ ID NO 31
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION
```

```
<400> SEQUENCE: 31

Gly Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 32
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = 4-hydroxyPro (4Hyp)
<220> FEATURE:
<221> NAME/KEY: MOD_RES
<222> LOCATION: (28)..(28)
<223> OTHER INFORMATION: AMIDATION

<400> SEQUENCE: 32

Gly Ser Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 33
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 33

Gly Ser Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 34
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MISC_FEATURE
<222> LOCATION: (9)..(9)
<223> OTHER INFORMATION: Xaa = beta-(4-pyridinyl)Ala (4Pal)
<220> FEATURE:
<221> NAME/KEY: MISC_FEATURE
<222> LOCATION: (12)..(12)
<223> OTHER INFORMATION: Xaa = alpha-aminoisobutyric acid (Aib)
<220> FEATURE:
<221> NAME/KEY: MISC_FEATURE
<222> LOCATION: (15)..(15)
<223> OTHER INFORMATION: Xaa = ornithine (Orn)
<220> FEATURE:
<221> NAME/KEY: MOD_RES
<222> LOCATION: (28)..(28)
<223> OTHER INFORMATION: AMIDATION

<400> SEQUENCE: 34

Gly Xaa Glu Phe Leu Ser Pro Glu Xaa Gln Arg Xaa Gln Gln Xaa Lys
1               5                   10                  15

Glu Ser Lys Lys Pro Pro Ala Lys Leu Gln Pro Arg
            20                  25

<210> SEQ ID NO 35
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with O-hexyl
<220> FEATURE:
<221> NAME/KEY: MOD_RES
<222> LOCATION: (28)..(28)
<223> OTHER INFORMATION: AMIDATION

<400> SEQUENCE: 35

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 36
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 36

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 37
<211> LENGTH: 28
<212> TYPE: PRT
<213> ORGANISM: Artificial Sequence
<220> FEATURE:
<223> OTHER INFORMATION: Ghrelin Analogue
```

```
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 37

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 38
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 38

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-butyryl
<220> FEATURE:
<221> NAME/KEY: MOD_RES
<222> LOCATION: (28)..(28)
<223> OTHER INFORMATION: AMIDATION

<400> SEQUENCE: 39

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 40
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with isobutyryl
```

```
<220> FEATURE:
<221> NAME/KEY: MOD_RES
<222> LOCATION: (28)..(28)
<223> OTHER INFORMATION: AMIDATION

<400> SEQUENCE: 40

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 41
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (1)..(1)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 41

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 42
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with S(CH2)9CH3
<220> FEATURE:
<221> NAME/KEY: MOD_RES
<222> LOCATION: (28)..(28)
<223> OTHER INFORMATION: AMIDATION

<400> SEQUENCE: 42

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 43
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MOD_RES
<222> LOCATION: (28)..(28)
<223> OTHER INFORMATION: AMIDATION

<400> SEQUENCE: 43

Gly Ser Ser Phe Lys Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 44
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 44

Xaa Xaa Xaa Phe Lys
1               5

<210> SEQ ID NO 45
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal)
<220> FEATURE:
<221> NAME/KEY: MOD_RES
<222> LOCATION: (5)..(5)
<223> OTHER INFORMATION: AMIDATION

<400> SEQUENCE: 45

Xaa Xaa Xaa Xaa Lys
1               5

<210> SEQ ID NO 46
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
```

```
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = ornithine (Orn)
<220> FEATURE:
<221> NAME/KEY: MOD_RES
<222> LOCATION: (5)..(5)
<223> OTHER INFORMATION: AMIDATION

<400> SEQUENCE: 46

Xaa Xaa Xaa Xaa Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 47

Xaa Xaa Xaa Phe Lys
1               5

<210> SEQ ID NO 48
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = pentafluorophenylAla (Pff)
<220> FEATURE:
<221> NAME/KEY: MOD_RES
<222> LOCATION: (5)..(5)
<223> OTHER INFORMATION: AMIDATION

<400> SEQUENCE: 48

Xaa Xaa Xaa Xaa Lys
1               5

<210> SEQ ID NO 49
```

```
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION

<400> SEQUENCE: 49

Xaa Xaa Xaa Xaa Lys
1               5

<210> SEQ ID NO 50
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 50

Xaa Xaa Xaa Xaa Lys
1               5

<210> SEQ ID NO 51
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta,beta-diphenylAla (D-Dip)
<220> FEATURE:
```

```
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 51

Xaa Xaa Xaa Phe Lys
1               5

<210> SEQ ID NO 52
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4-benzoylphenylAla (D-Bpa)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 52

Xaa Xaa Xaa Phe Lys
1               5

<210> SEQ ID NO 53
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-4-benzoylphenylAla (D-Bpa)
<220> FEATURE:
<221> NAME/KEY: MOD_RES
<222> LOCATION: (5)..(5)
<223> OTHER INFORMATION: AMIDATION

<400> SEQUENCE: 53

Xaa Xaa Xaa Phe Lys
1               5

<210> SEQ ID NO 54
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
```

```
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal)

<400> SEQUENCE: 54

Xaa Xaa Xaa Xaa
1

<210> SEQ ID NO 55
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-pyridiyl)Ala (4-Pal)

<400> SEQUENCE: 55

Xaa Xaa Xaa Xaa
1

<210> SEQ ID NO 56
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
```

```
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal)

<400> SEQUENCE: 56

Xaa Xaa Xaa Xaa
1

<210> SEQ ID NO 57
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-4,4'-biphenylAla (D-Bip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 57

Xaa Xaa Xaa Phe
1

<210> SEQ ID NO 58
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = O-bezyl-threonine (Thr(Bzl))
<220> FEATURE:
<221> NAME/KEY: MOD_RES
<222> LOCATION: (4)..(4)
<223> OTHER INFORMATION: AMIDATION

<400> SEQUENCE: 58

Xaa Xaa Xaa Xaa
1

<210> SEQ ID NO 59
<211> LENGTH: 4
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = pentafluorophenylAla (Pff)

<400> SEQUENCE: 59

Xaa Xaa Xaa Xaa
1

<210> SEQ ID NO 60
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi)

<400> SEQUENCE: 60

Xaa Xaa Xaa Xaa
1

<210> SEQ ID NO 61
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
```

```
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala (Taz)

<400> SEQUENCE: 61

Xaa Xaa Xaa Xaa
1

<210> SEQ ID NO 62
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta,beta-diphenylAla (D-Dip)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 62

Xaa Xaa Xaa Phe
1

<210> SEQ ID NO 63
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-beta,beta-diphenylAla (D-Dip)
<220> FEATURE:
<221> NAME/KEY: MOD_RES
<222> LOCATION: (4)..(4)
<223> OTHER INFORMATION: AMIDATION

<400> SEQUENCE: 63

Xaa Xaa Xaa Phe
1

<210> SEQ ID NO 64
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
```

```
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 64

Xaa Xaa Xaa Phe
1

<210> SEQ ID NO 65
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-3-benzothienylAla (D-Bal)
<220> FEATURE:
<221> NAME/KEY: MOD_RES
<222> LOCATION: (4)..(4)
<223> OTHER INFORMATION: AMIDATION

<400> SEQUENCE: 65

Xaa Xaa Xaa Phe
1

<210> SEQ ID NO 66
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(3-pyridiyl)Ala (3-Pal)
<220> FEATURE:
<221> NAME/KEY: MOD_RES
<222> LOCATION: (5)..(5)
<223> OTHER INFORMATION: AMIDATION

<400> SEQUENCE: 66

Xaa Xaa Xaa Xaa Lys
1               5
```

```
<210> SEQ ID NO 67
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (3)..(3)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (4)..(4)
<223> OTHER INFORMATION: Xaa = 2'-(4-phenyl)imidazolyl (psi-Pim)

<400> SEQUENCE: 67

Xaa Xaa Xaa Xaa
1

<210> SEQ ID NO 68
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION

<400> SEQUENCE: 68

Xaa Xaa Xaa Xaa Lys
1               5

<210> SEQ ID NO 69
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
```

```
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 69

Xaa Xaa Xaa Phe Lys
1               5

<210> SEQ ID NO 70
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION

<400> SEQUENCE: 70

Xaa Xaa Xaa Xaa Lys
1               5

<210> SEQ ID NO 71
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 71

Xaa Xaa Xaa Phe Xaa
1               5

<210> SEQ ID NO 72
<211> LENGTH: 5
```

```
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 72

Xaa Xaa Xaa Phe Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = Apc
<220> FEATURE:
<221> NAME/KEY: MOD_RES
<222> LOCATION: (5)..(5)
<223> OTHER INFORMATION: AMIDATION

<400> SEQUENCE: 73

Xaa Xaa Xaa Phe Xaa
1               5

<210> SEQ ID NO 74
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
```

```
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 74

Xaa Xaa Xaa Phe Lys
1               5

<210> SEQ ID NO 75
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION

<400> SEQUENCE: 75

Xaa Xaa Xaa Xaa Lys
1               5

<210> SEQ ID NO 76
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi)

<400> SEQUENCE: 76

Xaa Xaa Xaa Xaa
1

<210> SEQ ID NO 77
```

```
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 77

Xaa Xaa Xaa Phe
1

<210> SEQ ID NO 78
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = psi-2'-(4-phenyl)imidazolyl (psi-Pim)

<400> SEQUENCE: 78

Xaa Xaa Xaa Xaa
1

<210> SEQ ID NO 79
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = psi-2'-(4-phenyl)imidazolyl (psi-Pim)
```

```
<400> SEQUENCE: 79

Xaa Xaa Xaa Xaa
1

<210> SEQ ID NO 80
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = psi-2'-(4-phenyl)imidazolyl (psi-Pim)

<400> SEQUENCE: 80

Xaa Xaa Xaa Xaa
1

<210> SEQ ID NO 81
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (H-Aib)
<220> FEATURE:
<221> NAME/KEY: MISC_FEATURE
<222> LOCATION: (2)..(2)
<223> OTHER INFORMATION: Xaa = D-O-bezyl-serine (D-Ser(Bzl))
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = psi-2'-(4-phenyl)imidazolyl (psi-Pim)

<400> SEQUENCE: 81

Xaa Xaa Xaa Xaa
1

<210> SEQ ID NO 82
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
```

```
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala  (Taz)
<220> FEATURE:
<221> NAME/KEY: MOD_RES
<222> LOCATION: (5)..(5)
<223> OTHER INFORMATION: AMIDATION

<400> SEQUENCE: 82

Xaa Xaa Xaa Xaa Lys
1               5

<210> SEQ ID NO 83
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala  (Taz)
<220> FEATURE:
<221> NAME/KEY: MOD_RES
<222> LOCATION: (5)..(5)
<223> OTHER INFORMATION: AMIDATION

<400> SEQUENCE: 83

Xaa Xaa Xaa Xaa Lys
1               5

<210> SEQ ID NO 84
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 84

Xaa Xaa Xaa Xaa Lys
```

```
1               5

<210> SEQ ID NO 85
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION

<400> SEQUENCE: 85

Xaa Xaa Xaa Xaa Lys
1               5

<210> SEQ ID NO 86
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION

<400> SEQUENCE: 86

Xaa Xaa Xaa Xaa Lys
1               5

<210> SEQ ID NO 87
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
```

```
<221> NAME/KEY: MISC_FEATURE
<222> LOCATION: (2)..(2)
<223> OTHER INFORMATION: Xaa = D-3-benzothienylAla  (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 87

Xaa Xaa Xaa Phe Lys
1               5

<210> SEQ ID NO 88
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 88

Xaa Xaa Xaa Phe Xaa
1               5

<210> SEQ ID NO 89
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 89
```

Xaa Xaa Xaa Phe Xaa
1               5

<210> SEQ ID NO 90
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 90

Xaa Xaa Xaa Phe Xaa
1               5

<210> SEQ ID NO 91
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-beta-(2-naphthyl)-L-Ala (D-2-Nal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 91

Xaa Xaa Xaa Phe Xaa
1               5

<210> SEQ ID NO 92
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc

```
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal)
<220> FEATURE:
<221> NAME/KEY: MOD_RES
<222> LOCATION: (5)..(5)
<223> OTHER INFORMATION: AMIDATION

<400> SEQUENCE: 92

Xaa Xaa Xaa Phe Lys
1               5

<210> SEQ ID NO 93
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 93

Xaa Xaa Xaa Phe Xaa
1               5

<210> SEQ ID NO 94
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa =  D-beta-(2-naphthyl)-L-Ala (D-2-Nal)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 94
```

```
Xaa Xaa Xaa Phe Xaa
1               5

<210> SEQ ID NO 95
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-beta-(2-naphthyl)-L-Ala (D-2-Nal)
<220> FEATURE:
<221> NAME/KEY: MOD_RES
<222> LOCATION: (5)..(5)
<223> OTHER INFORMATION: AMIDATION

<400> SEQUENCE: 95

Xaa Xaa Xaa Phe Lys
1               5

<210> SEQ ID NO 96
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi)

<400> SEQUENCE: 96

Xaa Xaa Xaa Xaa
1

<210> SEQ ID NO 97
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
```

```
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION

<400> SEQUENCE: 97

Xaa Xaa Xaa Phe
1

<210> SEQ ID NO 98
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala  (Taz)

<400> SEQUENCE: 98

Xaa Xaa Xaa Xaa
1

<210> SEQ ID NO 99
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi)

<400> SEQUENCE: 99

Xaa Xaa Xaa Xaa
1
```

```
<210> SEQ ID NO 100
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala (Taz)

<400> SEQUENCE: 100

Xaa Xaa Xaa Xaa
1

<210> SEQ ID NO 101
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(2-thienyl)Ala (2-Thi)

<400> SEQUENCE: 101

Xaa Xaa Xaa Xaa
1

<210> SEQ ID NO 102
<211> LENGTH: 4
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
```

```
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (4)..(4)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = beta-(4-thiazolyl)Ala (Taz)

<400> SEQUENCE: 102

Xaa Xaa Xaa Xaa
1

<210> SEQ ID NO 103
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala  (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 103

Xaa Xaa Xaa Xaa Xaa
1               5

<210> SEQ ID NO 104
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa =  D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala  (Taz)
```

```
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 104

Xaa Xaa Xaa Xaa Xaa
1               5

<210> SEQ ID NO 105
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 105

Xaa Xaa Xaa Xaa Xaa
1               5

<210> SEQ ID NO 106
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-thiazolyl)Ala (Taz)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
```

```
<222> LOCATION: (5)..(5)
<223> OTHER INFORMATION: Xaa = Apc

<400> SEQUENCE: 106

Xaa Xaa Xaa Xaa Xaa
1               5

<210> SEQ ID NO 107
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(4-pyridiyl)Ala (4-Pal)
<220> FEATURE:
<221> NAME/KEY: MOD_RES
<222> LOCATION: (5)..(5)
<223> OTHER INFORMATION: AMIDATION

<400> SEQUENCE: 107

Xaa Xaa Xaa Xaa Lys
1               5

<210> SEQ ID NO 108
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(2-naphthyl)-L-Ala (D-2-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = O-bezyl-threonine (Thr(Bzl))
<220> FEATURE:
<221> NAME/KEY: MOD_RES
<222> LOCATION: (5)..(5)
<223> OTHER INFORMATION: AMIDATION

<400> SEQUENCE: 108

Xaa Xaa Xaa Xaa Lys
1               5

<210> SEQ ID NO 109
<211> LENGTH: 5
<212> TYPE: PRT
<213> ORGANISM: Artificial Sequence
<220> FEATURE:
```

```
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-beta-(1-naphthyl)-L-Ala (D-1-Nal)
<220> FEATURE:
<221> NAME/KEY: MOD_RES
<222> LOCATION: (5)..(5)
<223> OTHER INFORMATION: AMIDATION

<400> SEQUENCE: 109

Xaa Xaa Xaa Phe Lys
1               5

<210> SEQ ID NO 110
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 110

Xaa Xaa Xaa Xaa Xaa
1               5

<210> SEQ ID NO 111
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Inp
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
```

```
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 111

Xaa Xaa Xaa Xaa Xaa
1               5

<210> SEQ ID NO 112
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 112

Xaa Xaa Xaa Xaa Xaa
1               5

<210> SEQ ID NO 113
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-3-benzothienylAla (D-Bal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MISC_FEATURE
<222> LOCATION: (4)..(4)
<223> OTHER INFORMATION: Xaa = beta-(2-thienyl)Ala (2-Thi)
<220> FEATURE:
<221> NAME/KEY: MOD_RES
<222> LOCATION: (5)..(5)
```

```
<223> OTHER INFORMATION: AMIDATION
<220> FEATURE:
<221> NAME/KEY: MISC_FEATURE
<222> LOCATION: (5)..(5)
<223> OTHER INFORMATION: Xaa = Apc

<400> SEQUENCE: 113

Xaa Xaa Xaa Xaa Xaa
1               5

<210> SEQ ID NO 114
<211> LENGTH: 5
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = H-Apc
<220> FEATURE:
<221> NAME/KEY: MISC_FEATURE
<222> LOCATION: (2)..(2)
<223> OTHER INFORMATION: Xaa = D-beta-(1-naphthyl)-L-Ala (D-1-Nal)
<220> FEATURE:
<221> NAME/KEY: MISC_FEATURE
<222> LOCATION: (3)..(3)
<223> OTHER INFORMATION: Xaa = D-Trp
<220> FEATURE:
<221> NAME/KEY: MOD_RES
<222> LOCATION: (5)..(5)
<223> OTHER INFORMATION: AMIDATION

<400> SEQUENCE: 114

Xaa Xaa Xaa Phe Lys
1               5

<210> SEQ ID NO 115
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modfied with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modfied with NH-hexyl
<220> FEATURE:
<221> NAME/KEY: MOD_RES
<222> LOCATION: (28)..(28)
<223> OTHER INFORMATION: AMIDATION

<400> SEQUENCE: 115

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 116
<211> LENGTH: 28
<212> TYPE: PRT
```

```
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 116

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 117
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = 1-Apc
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 117

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 118
<211> LENGTH: 28
<212> TYPE: PRT
<213> ORGANISM: Artificial Sequence
<220> FEATURE:
<223> OTHER INFORMATION: Ghrelin analog
<220> FEATURE:
<221> NAME/KEY: MISC_FEATURE
<222> LOCATION: (1)..(1)
<223> OTHER INFORMATION: Xaa = Inp
<220> FEATURE:
```

```
<221> NAME/KEY: MOD_RES
<222> LOCATION: (28)..(28)
<223> OTHER INFORMATION: AMIDATION

<400> SEQUENCE: 118

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 119
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 119

Xaa Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 120
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 120

Xaa Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 121
<211> LENGTH: 28
<212> TYPE: PRT
<213> ORGANISM: Artificial Sequence
<220> FEATURE:
<223> OTHER INFORMATION: Ghrelin Analogue
<220> FEATURE:
```

```
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 121

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 122
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 122

Xaa Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 123
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION
```

```
<400> SEQUENCE: 123

Xaa Xaa Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 124
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = Inp
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 124

Xaa Ser Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 125
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MOD_RES
<222> LOCATION: (3)..(3)
<223> OTHER INFORMATION: modified with NH-heptyl
<220> FEATURE:
<221> NAME/KEY: MOD_RES
<222> LOCATION: (28)..(28)
<223> OTHER INFORMATION: AMIDATION

<400> SEQUENCE: 125

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 126
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (2)..(2)
<223> OTHER INFORMATION: Xaa = des-Ser
<220> FEATURE:
<221> NAME/KEY: MOD_RES
<222> LOCATION: (28)..(28)
<223> OTHER INFORMATION: AMIDATION

<400> SEQUENCE: 126

Gly Xaa Ser Phe Leu Ser Pro Glu His Gln Arg Val Gln Gln Arg Lys
1               5                   10                  15
```

```
Glu Ser Lys Lys Pro Pro Ala Lys Leu Gln Pro Arg
            20                  25

<210> SEQ ID NO 127
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MISC_FEATURE
<222> LOCATION: (1)..(1)
<223> OTHER INFORMATION: Xaa = des-Gly
<220> FEATURE:
<221> NAME/KEY: MISC_FEATURE
<222> LOCATION: (2)..(2)
<223> OTHER INFORMATION: Xaa = des-Ser
<220> FEATURE:
<221> NAME/KEY: MOD_RES
<222> LOCATION: (28)..(28)
<223> OTHER INFORMATION: AMIDATION

<400> SEQUENCE: 127

Xaa Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 128
<211> LENGTH: 28
<212> TYPE: PRT
<213> ORGANISM: Artificial Sequence
<220> FEATURE:
<223> OTHER INFORMATION: Ghrelin Analogue
<220> FEATURE:
<221> NAME/KEY: MISC_FEATURE
<222> LOCATION: (1)..(1)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 128

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 129
<211> LENGTH: 28
<212> TYPE: PRT
<213> ORGANISM: Artificial sequence
<220> FEATURE:
<223> OTHER INFORMATION: Ghrelin analog
<220> FEATURE:
<221> NAME/KEY: MOD_RES
<222> LOCATION: (3)..(3)
<223> OTHER INFORMATION: modified with O-hexyl
<220> FEATURE:
<221> NAME/KEY: MOD_RES
<222> LOCATION: (28)..(28)
<223> OTHER INFORMATION: AMIDATION

<400> SEQUENCE: 129

Gly Ser Asp Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```